United States Patent
Figg et al.

(10) Patent No.: US 8,835,115 B2
(45) Date of Patent: Sep. 16, 2014

(54) ABCB1 GENOTYPING TO PREDICT MICROTUBULE-STABILIZING-AGENT-INDUCED TOXICITY

(75) Inventors: William D. Figg, Fairfax, VA (US); Klaus Mross, Freiburg (DE); Dirk Behringer, Bochum (DE); Alex Sparreboom, Memphis, TN (US); Tristan Sissung, Annandale, VA (US); Stephan Mielke, Loehne (DE)

(73) Assignees: The United States of America as represented by the Secretary, Department of Health and Human Services, Washington, DC (US); Universitätsklinikum Freiburg, Freiburg (DE)

(*) Notice: Subject to any disclaimer, the term of this patent is extended or adjusted under 35 U.S.C. 154(b) by 715 days.

(21) Appl. No.: 12/304,071

(22) PCT Filed: Jul. 13, 2007

(86) PCT No.: PCT/US2007/073497
§ 371 (c)(1),
(2), (4) Date: Dec. 9, 2008

(87) PCT Pub. No.: WO2008/008976
PCT Pub. Date: Jan. 17, 2008

(65) Prior Publication Data
US 2010/0247481 A1 Sep. 30, 2010

Related U.S. Application Data

(60) Provisional application No. 60/807,453, filed on Jul. 14, 2006.

(51) Int. Cl.
*C07H 21/04* (2006.01)
*C12Q 1/68* (2006.01)

(52) U.S. Cl.
CPC ........ *C12Q 1/6883* (2013.01); *C12Q 2600/156* (2013.01); *C12Q 2600/106* (2013.01); *C12Q 2600/158* (2013.01); *C12Q 2600/172* (2013.01)
USPC ....... 435/6.11; 435/6.12; 435/91.1; 435/91.2; 536/23.1; 536/24.3; 536/12

(58) Field of Classification Search
None
See application file for complete search history.

(56) References Cited

U.S. PATENT DOCUMENTS

| | | |
|---|---|---|
| 6,617,450 B1 | 9/2003 | Stocker et al. |
| 6,753,177 B1 | 6/2004 | Stocker et al. |
| 6,855,812 B2 | 2/2005 | Hanscom et al. |
| 7,018,816 B2 | 3/2006 | Yates et al. |
| 2004/0191785 A1 | 9/2004 | Brinkmann et al. |
| 2004/0191822 A1 | 9/2004 | Yates et al. |
| 2004/0265896 A1 | 12/2004 | Mealey et al. |
| 2006/0024685 A1 | 2/2006 | Ho et al. |
| 2009/0325156 A1* | 12/2009 | Figg et al. .......... 435/6 |

FOREIGN PATENT DOCUMENTS

| | | |
|---|---|---|
| EP | 1 669 447 A1 | 6/2006 |
| WO | WO 2005/108605 A2 | 11/2005 |

OTHER PUBLICATIONS

Calado et al. (Br. J. of Haematology, vol. 117, pp. 768-774, 2002).*
Plasschaert et al. (Clinical Pharmacoogy & Therapeutics, vol. 76, No. 3, pp. 220-220, 2004).*
Babaoglu et al. (Clinical Pharmacology & Therapeutics, vol. 78, No. 6, pp. 619-626, 2005).*
Tran et al. (Clinical Pharmacology & Therapeutics, vol. 79, No. 6, pp. 570-580, 2006).*
Cote et al. (Cancer Therapy: Clinical, vol. 13, No. 11, pp. 3269-3275, 2007).*
Han et al. (Cancer, vol. 110, No. 1, pp. 138-147, 2007).*
Tsai et al. (Clinica Chimica Acta, vol. 404, pp. 160-165, 2009.*
Rizzo et al. (Breast Cancer Res Treat, vol. 124, pp. 593-598, 2010).*
Leskela et al. (Pharmacogenomics, Journal, pp. 1-9, 2010).*
Ofverholm et al. (Oncology Letters, vol. 1, pp. 151-154, 2010).*
Gonzalez-Haba et al. (Future Medicine, Issn 1462-2416, 2010).*
Sissung et al. (Eur. J. of Cancer, vol. 42, 2893-96, 2006).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Thisted (May 1998).*
Nollau et al. (Clinical Chemistry, vol. 43, No. 7, pp. 1114-1128, 1997).*
NCBI, dbSNP rs2032582, Jan. 28, 2001.*
Carpinteiro et al., "Genetic Protection of Repopulating Hematopoietic Cells with an Improved MDR1-Retrovirus Allows Administration of Intensified Chemotherapy Following Stem Cell Transplantation in Mice," *Int. J Cancer* 98:785-792, 2002.
de Jong et al., "Role of Pharmacogenetics in Irinotecan Therapy," *Cancer Lett.* 234:90-106, 2006 (Epub 2005).

(Continued)

*Primary Examiner* — Jeanine A Goldberg
(74) *Attorney, Agent, or Firm* — Klarquist Sparkman, LLP

(57) ABSTRACT

The present disclosure provides methods of identifying subjects having an increased likelihood of developing one or more adverse side effects resulting from administration of a microtubule-stabilizing agent. In particular examples, the method includes determining whether the subject has an ABCB1 predictive polymorphism for microtubule-stabilizing agent-induced toxicity, wherein the presence of such a polymorphism indicates that the subject has an increased risk of developing microtubule-stabilizing agent induced adverse effects. Examples of ABCB1 predictive polymorphisms include 2677G>T/A and 3435C>T. Also provided are methods of modifying microtubule-stabilizing agent therapy in a subject identified as having one or more ABCB1 predictive polymorphisms. Kits and isolated nucleic acid molecules that can be used in the disclosed methods are also provided.

14 Claims, 2 Drawing Sheets

(56) References Cited

OTHER PUBLICATIONS

Kemper et al., "Improved Penetration of Docetaxel into the Brain by Co-Administration of Inhibitors of P-Glycoprotein," *Eur. J. Cancer* 40:1269-1274, 2004.
Kim et al., "Identification of Functionally Variant MDR1 Alleles Among European Americans and African Americans," *Clin. Pharmacol. Ther.* 70:189-199, 2001.
Lepper et al., "Mechanisms of Resistance to Anticancer Drugs: The Role of the Polymorphic ABC Transporters ABCB1 and ABCG2," *Pharmacogenomics* 6:115-138, 2005.
Rowinsky et al., "Phase I and Pharmacokinetic Study of Paclitaxel in Combination with Biricodar, a Novel Agent that Reverses Multidrug Resistance Conferred by Overexpression of Both MDR1 and MRP," *J. Clin. Oncol.* 16:2964-2976, 1998.
Sakaeda et al., "Pharmacogenetics of Drug Transporters and its Impact on the Pharmacotherapy," *Curr. Top. Med..Chem.* 4:1383-1396, 2004.
Seiden et al., "A Phase II Study of the MDR Inhibitor Biricodar (INCEL, VX-710) and Paclitaxel in Women with Advanced Ovarian Cancer Refractory to Paclitaxel Therapy," *Gynecol. Oncol.* 86:302-310, 2002.
Sunder-Plassmann et al., "Simultaneous Analysis of MDR1 C3435T, G2677T/A, and C1236T Genotypes by Multiplexed Mutagenically Separated PCR," *Clin. Chem.. Lab. Med.* 43:192-194, 2005.
Wang et al., "Multidrug Resistance Polypeptide 1 (MDR1, ABCB1) Variant 3435C>T Affects mRNA Stability," *Pharmacogenet. Genomics* 15:693-704, 2005.
Fracasso et al., "Phase II Study of Paclitaxel and Valspodar (PSC 833) in Refractory Ovarian Carcinoma: A Gynecologic Oncology Group Study," *J. Clin. Oncol.* 19:2975-2982, 2001.
Fruehauf et al., "Protection of Hematopoietic Stem Cells from Chemotherapy-Induced Toxicity by Multidrug-Resistance 1 Gene Transfer," *Recent Results Cancer Res.* 144:93-115, 1998.
Goodin et al., "Epothilones: Mechanism of Action and Biologic Activity," *J. Clin. Oncol.* 22:2015-2025, 2004.
Gréen et al., "*mdr-1* Single Nucleotide Polymorphisms in Ovarian Cancer Tissue: G2677T/A Correlates with Response to Paclitaxel Chemotherapy," *Clin. Cancer Res.* 12:854-859, 2006.
He et al., "Novel Molecules that Interact with Microtubules and Have Functional Activity Similar to Taxol™," *Drug Discov. Today* 6:1153-1164, 2001.
Hitzl et al., "The C3435T Mutation in the Human *MDR1* Gene is Associated with Altered Efflux of the P-Glycoprotein Substrate Rhodamine 123 from CD56+ Natural Killer Cells," *Pharmacogenetics* 11:293-298, 2001.
Hoffmeyer et al., "Functional Polymorphisms of the Human Multidrug-Resistance Gene: Multiple Sequence Variations and Correlation of One Allele with P-Glycoprotein Expression and Activity In Vivo," *Proc. Natl. Acad. Sci. USA* 97:3473-3478, 2000.
Ieire et al., "The *MDR1* (ABCB1) Gene Polymorphism and its Clinical Implications," *Clin. Pharmacokinet.* 43:553-576, 2004.
Komrokji and Lyman, "The Colony-Stimulating Factors: Use to Prevent and Treat Neutropenia and its Complications," *Expert Opin. Biol. Ther.* 4:1897-1910, 2004.
Lee et al., "BMS-247550: A Novel Epothilone Analog with a Mode of Action Similar to Paclitaxel but Possessing Superior Antitumor Efficacy," *Clin. Cancer Res.* 7:1429-1437, 2001.
Lee and Swain, "Peripheral Neuropathy Induced by Microtubule-Stabilizing Agents," *J. Clin. Oncol.* 24:1633-1642, 2006.
Mickley et al., "Genetic Polymorphism in *MDR-1*: A Tool for Examining Allelic Expression in Normal Cells, Unselected and Drug-Selected Cell Lines, and Human Tumors," *Blood* 91:1749-1756, 1998.

Nakajima et al., "Pharmacokinetics of Paclitaxel in Ovarian Cancer Patients and Genetic Polymorphisms of CYP2C8, CYP3A4, and MDR1," *J. Clin. Pharmacol.* 45:674-682, 2005.
Owen et al., "Relationship Between the $C_{3435}T$ and $G_{2677}T(A)$ Polymorphisms in the *ABCB1* Gene and P-Glycoprotein Expression in Human Liver," *Br. J. Clin. Pharmacol.* 59:365-370, 2005.
Sakaeda, "*MDR1* Genotype-Related Pharmacokinetics: Fact or Fiction?," *Drug Metab. Pharmacokinet.* 20:391-414, 2005.
Sissung et al., "Association of *ABCB1* Genotypes with Paclitaxel-Mediated Peripheral Neuropathy and Neutropenia," *Eur. J Cancer* 42:2893-2896, 2006.
Smith et al., "Paclitaxel-Induced Neuropathic Hypersensitivity in Mice: Response in 10 Inbred Mouse Strains," *Life Sci.* 74:2593-2604, 2004.
Smith et al., "2006 Update of Recommendations for the Use of White Blood Cell Growth Factors: An Evidence-Based Clinical Practice Guideline," *J. Clin. Oncol.* 24:3187-3205, 2006.
Song et al., "G2677T and C3435T Genotype and Haplotype are Associated With Hepatic *ABCB1* (*MDR1*) Expression," *J. Clin. Pharmacol.* 46:373-379, 2006.
Toppmeyer et al., "Safety and Efficacy of the Multidrug Resistance Inhibitor Incel (Biricodar; VX-710) in Combination with Paclitaxel for Advanced Breast Cancer Refractory to Paclitaxel," *Clin. Cancer Res.* 8:670-678, 2002.
Tran et al., "Pharmacokinetics and Toxicity of Docetaxel: Role of CYP3A, MDR1, and GST Polymorphisms," *Clin. Pharmacol. Ther.* 79:570-580, 2006.
Vahdat et al., "Reduction of Paclitaxel-Induced Peripheral Neuropathy with Glutamine," *Clin. Cancer Res.* 7:1192-1197, 2001.
Yamauchi et al., "Neurotoxicity Induced by Tacrolimus After Liver Transplantation: Relation to Genetic Polymorphisms of the *ABCB1* (*MDR1*) Gene," *Transplantation* 74:571-573, 2002.
Yamaguchi et al., "Genetic Variation in *ABCB1* Influences Paclitaxel Pharmacokinetics in Japanese Patients with Ovarian Cancer," *Int. J. Gynecol. Cancer* 16:979-985, 2006.
Yi et al., "A Variant 2677A Allele of the *MDR1* Gene Affects Fexofenadine Disposition," *Clin. Pharmacol. Ther.* 76:418-427, 2004.
Aventis Pharmaceuticals Inc. Package Insert for Taxotere®.
Bristol-Myers Squibb Company Package Insert for Taxol®.
BioxelPharma Inc., "Products and Projects," http://www.bioxelpharma.com/en/produits.php, printed Jun. 14, 2006.
Cancer Medicine, "Novel Compounds Targeting Microtubules and Related Organelles," http://www.ncbi/nlm.nih.gov/entrez/query.fcgi?cmd=Search&db=books&doptcmdl=GenB..., printed Jun. 27, 2006.
Cancer Medicine, Section 12: Chemotherapeutic Agents, Microtubule-Targeting Natural Products, http://www.ncbi.nlm.nih.gov/entrez/query.fcgi?cmd=search&db=books&doptcmdl=GenB..., printed Jun. 21, 2006.
Cancer Medicine, Section 12: Chemotherapeutic Agents, Microtubule-Targeting Natural Products, Figure 53-3. Chemical Structures of the Taxanes Paclitaxel and Docetaxel, http://www.ncbi.nlm.nih.giv/books/bv.fcgi?rid=cmed6.figgrp.13331, printed Jun. 21, 2006.
Cancer Medicine, Section 12: Chemotherapeutic Agents, Microtubule-Targeting Natural Products, Table 53-2. Comparative Pharmacokinetic and Toxicologic Characteristics, http://www.ncbi.nlm.nih.giv/books/bv.fcgi?rid=cmed6.table.13336, printed Jun. 21, 2006.
National Cancer Institute, "Taxanes in Cancer Treatment," CancerMail from the National Cancer Institute, http://cancerweb.ncl.ac.uk/cancernet/600715.html, printed Jun. 14, 2006.

* cited by examiner

SEQUENCE LISTING

<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide PCR primer.

<400> SEQUENCE: 1
gttcacttca gttacccatc tcg                                          23

<210> SEQ ID NO 2
<211> LENGTH: 23
<212> TYPE: DNA
<213> ORGANISM: Artificial Sequence
<220> FEATURE:
<223> OTHER INFORMATION: Oligonucleotide PCR primer.

<400> SEQUENCE: 2
tatcctgtcc atcaacactg acc                                          23

<210> SEQ ID NO 3
<211> LENGTH: 22
<212> TYPE: DNA
<213> ORGANISM: Artificial Sequence
<220> FEATURE:
<223> OTHER INFORMATION: Oligonucleotide PCR primer.

-continued

```
<400> SEQUENCE: 3
aggctatagg ttccaggctt gc                                              22

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide PCR primer.

<400> SEQUENCE: 4
agaacagtgt gaagacaatg gcc                                             23

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide PCR primer.

<400> SEQUENCE: 5
atctcacagt aacttggcag tttc                                            24

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide PCR primer.

<400> SEQUENCE: 6
aacccaaaca ggaagtgtgg cc                                              22

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide sequencing primer.

<400> SEQUENCE: 7
gtcagttcct atatcctgtg tctg                                            24

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide sequencing primer.

<400> SEQUENCE: 8
tcctgtccat caacactgac ctg                                             23

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide sequencing primer.

<400> SEQUENCE: 9
cccatcattg caatagcagg ag                                              22
```

-continued

<210> SEQ ID NO 10
<211> LENGTH: 23
<212> TYPE: DNA
<213> ORGANISM: Artificial Sequence
<220> FEATURE:
<223> OTHER INFORMATION: Oligonucleotide sequencing primer.

<400> SEQUENCE: 10
gaacagtgtg aagacaatgg cct                                           23

<210> SEQ ID NO 11
<211> LENGTH: 23
<212> TYPE: DNA
<213> ORGANISM: Artificial Sequence
<220> FEATURE:
<223> OTHER INFORMATION: Oligonucleotide sequencing primer.

<400> SEQUENCE: 11
gctggtcctg aagttgatct gtg                                           23

<210> SEQ ID NO 12
<211> LENGTH: 23
<212> TYPE: DNA
<213> ORGANISM: Artificial Sequence
<220> FEATURE:
<223> OTHER INFORMATION: Oligonucleotide sequencing primer.

<400> SEQUENCE: 12
aaacaggaag tgtggccaga tgc                                           23

<210> SEQ ID NO 13
<211> LENGTH: 3843
<212> TYPE: DNA
<213> ORGANISM: Homo Sapiens
<220> FEATURE:
<221> NAME/KEY: CDS
<222> LOCATION: (1)..(3843)

<400> SEQUENCE: 13

```
atg gat ctt gaa ggg gac cgc aat gga gga gca aag aag aag aac ttt      48
Met Asp Leu Glu Gly Asp Arg Asn Gly Gly Ala Lys Lys Lys Asn Phe
1               5                   10                  15 ttt aaa ctg aac aat aaa agt gaa aaa gat aag aag gaa aag aaa cca      96
Phe Lys Leu Asn Asn Lys Ser Glu Lys Asp Lys Lys Glu Lys Lys Pro
            20                  25                  30 act gtc agt gta ttt tca atg ttt cgc tat tca aat tgg ctt gac aag     144
Thr Val Ser Val Phe Ser Met Phe Arg Tyr Ser Asn Trp Leu Asp Lys
        35                  40                  45 ttg tat atg gtg gtg gga act ttg gct gcc atc atc cat ggg gct gga     192
Leu Tyr Met Val Val Gly Thr Leu Ala Ala Ile Ile His Gly Ala Gly
    50                  55                  60 ctt cct ctc atg atg ctg gtg ttt gga gaa atg aca gat atc ttt gca     240
Leu Pro Leu Met Met Leu Val Phe Gly Glu Met Thr Asp Ile Phe Ala
65                  70                  75                  80 aat gca gga aat tta gaa gat ctg atg tca aac atc act aat aga agt     288
Asn Ala Gly Asn Leu Glu Asp Leu Met Ser Asn Ile Thr Asn Arg Ser
                85                  90                  95 gat atc aat gat aca ggg ttc ttc atg aat ctg gag gaa gac atg acc     336
Asp Ile Asn Asp Thr Gly Phe Phe Met Asn Leu Glu Glu Asp Met Thr
            100                 105                 110 agg tat gcc tat tat tac agt gga att ggt gct ggg gtg ctg gtt gct     384
Arg Tyr Ala Tyr Tyr Tyr Ser Gly Ile Gly Ala Gly Val Leu Val Ala
        115                 120                 125
```

```
gct tac att cag gtt tca ttt tgg tgc ctg gca gct gga aga caa ata       432
Ala Tyr Ile Gln Val Ser Phe Trp Cys Leu Ala Ala Gly Arg Gln Ile
    130             135                 140 cac aaa att aga aaa cag ttt ttt cat gct ata atg cga cag gag ata       480
His Lys Ile Arg Lys Gln Phe Phe His Ala Ile Met Arg Gln Glu Ile
145             150                 155                 160 ggc tgg ttt gat gtg cac gat gtt ggg gag ctt aac acc cga ctt aca       528
Gly Trp Phe Asp Val His Asp Val Gly Glu Leu Asn Thr Arg Leu Thr
                165                 170                 175 gat gat gtc tcc aag att aat gaa gga att ggt gac aaa att gga atg       576
Asp Asp Val Ser Lys Ile Asn Glu Gly Ile Gly Asp Lys Ile Gly Met
                180                 185                 190 ttc ttt cag tca atg gca aca ttt ttc act ggg ttt ata gta gga ttt       624
Phe Phe Gln Ser Met Ala Thr Phe Phe Thr Gly Phe Ile Val Gly Phe
            195                 200                 205 aca cgt ggt tgg aag cta acc ctt gtg att ttg gcc atc agt cct gtt       672
Thr Arg Gly Trp Lys Leu Thr Leu Val Ile Leu Ala Ile Ser Pro Val
210             215                 220 ctt gga ctg tca gct gct gtc tgg gca aag ata cta tct tca ttt act       720
Leu Gly Leu Ser Ala Ala Val Trp Ala Lys Ile Leu Ser Ser Phe Thr
225             230                 235                 240 gat aaa gaa ctc tta gcg tat gca aaa gct gga gca gta gct gaa gag       768
Asp Lys Glu Leu Leu Ala Tyr Ala Lys Ala Gly Ala Val Ala Glu Glu
                245                 250                 255 gtc ttg gca gca att aga act gtg att gca ttt gga gga caa aag aaa       816
Val Leu Ala Ala Ile Arg Thr Val Ile Ala Phe Gly Gly Gln Lys Lys
                260                 265                 270 gaa ctt gaa agg tac aac aaa aat tta gaa gaa gct aaa aga att ggg       864
Glu Leu Glu Arg Tyr Asn Lys Asn Leu Glu Glu Ala Lys Arg Ile Gly
            275                 280                 285 ata aag aaa gct att aca gcc aat att tct ata ggt gct gct ttc ctg       912
Ile Lys Lys Ala Ile Thr Ala Asn Ile Ser Ile Gly Ala Ala Phe Leu
    290                 295                 300 ctg atc tat gca tct tat gct ctg gcc ttc tgg tat ggg acc acc ttg       960
Leu Ile Tyr Ala Ser Tyr Ala Leu Ala Phe Trp Tyr Gly Thr Thr Leu
305             310                 315                 320 gtc ctc tca ggg gaa tat tct att gga caa gta ctc act gta ttc ttt      1008
Val Leu Ser Gly Glu Tyr Ser Ile Gly Gln Val Leu Thr Val Phe Phe
                325                 330                 335 tct gta tta att ggg gct ttt agt gtt gga cag gca tct cca agc att      1056
Ser Val Leu Ile Gly Ala Phe Ser Val Gly Gln Ala Ser Pro Ser Ile
                340                 345                 350 gaa gca ttt gca aat gca aga gga gca gct tat gaa atc ttc aag ata      1104
Glu Ala Phe Ala Asn Ala Arg Gly Ala Ala Tyr Glu Ile Phe Lys Ile
            355                 360                 365 att gat aat aag cca agt att gac agc tat tcg aag agt ggg cac aaa      1152
Ile Asp Asn Lys Pro Ser Ile Asp Ser Tyr Ser Lys Ser Gly His Lys
    370                 375                 380 cca gat aat att aag gga aat ttg gaa ttc aga aat gtt cac ttc aat      1200
Pro Asp Asn Ile Lys Gly Asn Leu Glu Phe Arg Asn Val His Phe Asn
385             390                 395                 400 tac cca tct cga aaa gaa gtt aag atc ttg aag ggc ctg aac ctg aag      1248
Tyr Pro Ser Arg Lys Glu Val Lys Ile Leu Lys Gly Leu Asn Leu Lys
                405                 410                 415 gtg cag agt ggg cag acg gtg gcc ctg gtt gga aac agt ggc tgt ggg      1296
Val Gln Ser Gly Gln Thr Val Ala Leu Val Gly Asn Ser Gly Cys Gly
                420                 425                 430 aag agc aca aca gtc cag ctg atg cag agg ctc tat gac ccc aca gag      1344
Lys Ser Thr Thr Val Gln Leu Met Gln Arg Leu Tyr Asp Pro Thr Glu
            435                 440                 445
```

-continued

| | | |
|---|---|---|
| ggg atg gtc agt gtt gat gga cag gat att agg acc ata aat gta agg<br>Gly Met Val Ser Val Asp Gly Gln Asp Ile Arg Thr Ile Asn Val Arg<br>450                           455                       460 | 1392 | |
| ttt cta cgg gaa atc att ggt gtg gtg agt cag gaa cct gta ttg ttt<br>Phe Leu Arg Glu Ile Ile Gly Val Val Ser Gln Glu Pro Val Leu Phe<br>465                          470                       475                  480 | 1440 | |
| gcc acc acg ata gct gaa aac att cgc tat ggc cgt gaa aat gtc acc<br>Ala Thr Thr Ile Ala Glu Asn Ile Arg Tyr Gly Arg Glu Asn Val Thr<br>                    485                       490                       495 | 1488 | |
| atg gat gag att gag aaa gct gtc aag gaa gcc aat gcc tat gac ttt<br>Met Asp Glu Ile Glu Lys Ala Val Lys Glu Ala Asn Ala Tyr Asp Phe<br>                    500                       505                       510 | 1536 | |
| atc atg aaa ctg cct cat aaa ttt gac acc ctg gtt gga gag aga ggg<br>Ile Met Lys Leu Pro His Lys Phe Asp Thr Leu Val Gly Glu Arg Gly<br>               515                       520                       525 | 1584 | |
| gcc cag ttg agt ggt ggg cag aag cag agg atc gcc att gca cgt gcc<br>Ala Gln Leu Ser Gly Gly Gln Lys Gln Arg Ile Ala Ile Ala Arg Ala<br>530                           535                       540 | 1632 | |
| ctg gtt cgc aac ccc aag atc ctc ctg ctg gat gag gcc acg tca gcc<br>Leu Val Arg Asn Pro Lys Ile Leu Leu Leu Asp Glu Ala Thr Ser Ala<br>545                       550                       555                  560 | 1680 | |
| ttg gac aca gaa agc gaa gca gtg gtt cag gtg gct ctg gat aag gcc<br>Leu Asp Thr Glu Ser Glu Ala Val Val Gln Val Ala Leu Asp Lys Ala<br>                    565                       570                       575 | 1728 | |
| aga aaa ggt cgg acc acc att gtg ata gct cat cgt ttg tct aca gtt<br>Arg Lys Gly Arg Thr Thr Ile Val Ile Ala His Arg Leu Ser Thr Val<br>                    580                       585                       590 | 1776 | |
| cgt aat gct gac gtc atc gct ggt ttc gat gat gga gtc att gtg gag<br>Arg Asn Ala Asp Val Ile Ala Gly Phe Asp Asp Gly Val Ile Val Glu<br>               595                       600                       605 | 1824 | |
| aaa gga aat cat gat gaa ctc atg aaa gag aaa ggc att tac ttc aaa<br>Lys Gly Asn His Asp Glu Leu Met Lys Glu Lys Gly Ile Tyr Phe Lys<br>610                           615                       620 | 1872 | |
| ctt gtc aca atg cag aca gca gga aat gaa gtt gaa tta gaa aat gca<br>Leu Val Thr Met Gln Thr Ala Gly Asn Glu Val Glu Leu Glu Asn Ala<br>625                       630                       635                  640 | 1920 | |
| gct gat gaa tcc aaa agt gaa att gat gcc ttg gaa atg tct tca aat<br>Ala Asp Glu Ser Lys Ser Glu Ile Asp Ala Leu Glu Met Ser Ser Asn<br>                    645                       650                       655 | 1968 | |
| gat tca aga tcc agt cta ata aga aaa aga tca act cgt agg agt gtc<br>Asp Ser Arg Ser Ser Leu Ile Arg Lys Arg Ser Thr Arg Arg Ser Val<br>               660                       665                       670 | 2016 | |
| cgt gga tca caa gcc caa gac aga aag ctt agt acc aaa gag gct ctg<br>Arg Gly Ser Gln Ala Gln Asp Arg Lys Leu Ser Thr Lys Glu Ala Leu<br>               675                       680                       685 | 2064 | |
| gat gaa agt ata cct cca gtt tcc ttt tgg agg att atg aag cta aat<br>Asp Glu Ser Ile Pro Pro Val Ser Phe Trp Arg Ile Met Lys Leu Asn<br>690                           695                       700 | 2112 | |
| tta act gaa tgg cct tat ttt gtt gtt ggt gta ttt tgt gcc att ata<br>Leu Thr Glu Trp Pro Tyr Phe Val Val Gly Val Phe Cys Ala Ile Ile<br>705                           710                       715                  720 | 2160 | |
| aat gga ggc ctg caa cca gca ttt gca ata ata ttt tca aag att ata<br>Asn Gly Gly Leu Gln Pro Ala Phe Ala Ile Ile Phe Ser Lys Ile Ile<br>                    725                       730                       735 | 2208 | |
| ggg gtt ttt aca aga att gat gat cct gaa aca aaa cga cag aat agt<br>Gly Val Phe Thr Arg Ile Asp Asp Pro Glu Thr Lys Arg Gln Asn Ser<br>                    740                       745                       750 | 2256 | |
| aac ttg ttt tca cta ttg ttt cta gcc ctt gga att att tct ttt att<br>Asn Leu Phe Ser Leu Leu Phe Leu Ala Leu Gly Ile Ile Ser Phe Ile<br>               755                       760                       765 | 2304 | |

```
                                                       -continued aca ttt ttc ctt cag ggt ttc aca ttt ggc aaa gct gga gag atc ctc    2352
Thr Phe Phe Leu Gln Gly Phe Thr Phe Gly Lys Ala Gly Glu Ile Leu
        770                 775                 780 acc aag cgg ctc cga tac atg gtt ttc cga tcc atg ctc aga cag gat    2400
Thr Lys Arg Leu Arg Tyr Met Val Phe Arg Ser Met Leu Arg Gln Asp
785                 790                 795                 800 gtg agt tgg ttt gat gac cct aaa aac acc act gga gca ttg act acc    2448
Val Ser Trp Phe Asp Asp Pro Lys Asn Thr Thr Gly Ala Leu Thr Thr
                805                 810                 815 agg ctc gcc aat gat gct gct caa gtt aaa ggg gct ata ggt tcc agg    2496
Arg Leu Ala Asn Asp Ala Ala Gln Val Lys Gly Ala Ile Gly Ser Arg
            820                 825                 830 ctt gct gta att acc cag aat ata gca aat ctt ggg aca gga ata att    2544
Leu Ala Val Ile Thr Gln Asn Ile Ala Asn Leu Gly Thr Gly Ile Ile
                835                 840                 845 ata tcc ttc atc tat ggt tgg caa cta aca ctg tta ctc tta gca att    2592
Ile Ser Phe Ile Tyr Gly Trp Gln Leu Thr Leu Leu Leu Leu Ala Ile
        850                 855                 860 gta ccc atc att gca ata gca gga gtt gtt gaa atg aaa atg ttg tct    2640
Val Pro Ile Ile Ala Ile Ala Gly Val Val Glu Met Lys Met Leu Ser
865                 870                 875                 880 gga caa gca ctg aaa gat aag aaa gaa cta gaa ggt gct ggg aag atc    2688
Gly Gln Ala Leu Lys Asp Lys Lys Glu Leu Glu Gly Ala Gly Lys Ile
                885                 890                 895 gct act gaa gca ata gaa aac ttc cga acc gtt gtt tct ttg act cag    2736
Ala Thr Glu Ala Ile Glu Asn Phe Arg Thr Val Val Ser Leu Thr Gln
            900                 905                 910 gag cag aag ttt gaa cat atg tat gct cag agt ttg cag gta cca tac    2784
Glu Gln Lys Phe Glu His Met Tyr Ala Gln Ser Leu Gln Val Pro Tyr
                915                 920                 925 aga aac tct ttg agg aaa gca cac atc ttt gga att aca ttt tcc ttc    2832
Arg Asn Ser Leu Arg Lys Ala His Ile Phe Gly Ile Thr Phe Ser Phe
        930                 935                 940 acc cag gca atg atg tat ttt tcc tat gct gga tgt ttc cgg ttt gga    2880
Thr Gln Ala Met Met Tyr Phe Ser Tyr Ala Gly Cys Phe Arg Phe Gly
945                 950                 955                 960 gcc tac ttg gtg gca cat aaa ctc atg agc ttt gag gat gtt ctg tta    2928
Ala Tyr Leu Val Ala His Lys Leu Met Ser Phe Glu Asp Val Leu Leu
                965                 970                 975 gta ttt tca gct gtt gtc ttt ggt gcc atg gcc gtg ggg caa gtc agt    2976
Val Phe Ser Ala Val Val Phe Gly Ala Met Ala Val Gly Gln Val Ser
            980                 985                 990 tca ttt gct cct gac tat gcc aaa  gcc aaa ata tca gca  gcc cac atc   3024
Ser Phe Ala Pro Asp Tyr Ala Lys  Ala Lys Ile Ser Ala  Ala His Ile
                995                 1000                1005 atc atg  atc att gaa aaa acc  cct ttg att gac agc  tac agc acg       3069
Ile Met  Ile Ile Glu Lys Thr  Pro Leu Ile Asp Ser  Tyr Ser Thr
        1010                1015                1020 gaa ggc  cta atg ccg aac aca  ttg gaa gga aat gtc  aca ttt ggt       3114
Glu Gly  Leu Met Pro Asn Thr  Leu Glu Gly Asn Val  Thr Phe Gly
1025                1030                1035 gaa gtt  gta ttc aac tat ccc  acc cga ccg gac atc  cca gtg ctt       3159
Glu Val  Val Phe Asn Tyr Pro  Thr Arg Pro Asp Ile  Pro Val Leu
        1040                1045                1050 cag gga  ctg agc ctg gag gtg  aag aag ggc cag acg  ctg gct ctg       3204
Gln Gly  Leu Ser Leu Glu Val  Lys Lys Gly Gln Thr  Leu Ala Leu
        1055                1060                1065 gtg ggc  agc agt ggc tgt ggg  aag agc aca gtg gtc  cag ctc ctg       3249
Val Gly  Ser Ser Gly Cys Gly  Lys Ser Thr Val Val  Gln Leu Leu
1070                1075                1080
```

| | | | | | | | | | | | | |
|---|---|---|---|---|---|---|---|---|---|---|---|---|
| gag | cgg | ttc | tac | gac | ccc | ttg | gca | ggg | aaa | gtg | ctg | ctt gat ggc | 3294 |
| Glu | Arg | Phe | Tyr | Asp | Pro | Leu | Ala | Gly | Lys | Val | Leu | Leu Asp Gly |
| 1085 | | | | | 1090 | | | | | 1095 | | |

```
gag cgg ttc tac gac ccc ttg gca ggg aaa gtg ctg ctt gat ggc        3294
Glu Arg Phe Tyr Asp Pro Leu Ala Gly Lys Val Leu Leu Asp Gly
    1085            1090                1095 aaa gaa ata aag cga ctg aat gtt cag tgg ctc cga gca cac ctg        3339
Lys Glu Ile Lys Arg Leu Asn Val Gln Trp Leu Arg Ala His Leu
1100            1105                1110 ggc atc gtg tcc cag gag ccc atc ctg ttt gac tgc agc att gct        3384
Gly Ile Val Ser Gln Glu Pro Ile Leu Phe Asp Cys Ser Ile Ala
    1115            1120                1125 gag aac att gcc tat gga gac aac agc cgg gtg gtg tca cag gaa        3429
Glu Asn Ile Ala Tyr Gly Asp Asn Ser Arg Val Val Ser Gln Glu
1130            1135                1140 gag atc gtg agg gca gca aag gag gcc aac ata cat gcc ttc atc        3474
Glu Ile Val Arg Ala Ala Lys Glu Ala Asn Ile His Ala Phe Ile
    1145            1150                1155 gag tca ctg cct aat aaa tat agc act aaa gta gga gac aaa gga        3519
Glu Ser Leu Pro Asn Lys Tyr Ser Thr Lys Val Gly Asp Lys Gly
1160            1165                1170 act cag ctc tct ggt ggc cag aaa caa cgc att gcc ata gct cgt        3564
Thr Gln Leu Ser Gly Gly Gln Lys Gln Arg Ile Ala Ile Ala Arg
    1175            1180                1185 gcc ctt gtt aga cag cct cat att ttg ctt ttg gat gaa gcc acg        3609
Ala Leu Val Arg Gln Pro His Ile Leu Leu Leu Asp Glu Ala Thr
1190            1195                1200 tca gct ctg gat aca gaa agt gaa aag gtt gtc caa gaa gcc ctg        3654
Ser Ala Leu Asp Thr Glu Ser Glu Lys Val Val Gln Glu Ala Leu
    1205            1210                1215 gac aaa gcc aga gaa ggc cgc acc tgc att gtg att gct cac cgc        3699
Asp Lys Ala Arg Glu Gly Arg Thr Cys Ile Val Ile Ala His Arg
1220            1225                1230 ctg tcc acc atc cag aat gca gac tta ata gtg gtg ttt cag aat        3744
Leu Ser Thr Ile Gln Asn Ala Asp Leu Ile Val Val Phe Gln Asn
    1235            1240                1245 ggc aga gtc aag gag cat ggc acg cat cag cag ctg ctg gca cag        3789
Gly Arg Val Lys Glu His Gly Thr His Gln Gln Leu Leu Ala Gln
1250            1255                1260 aaa ggc atc tat ttt tca atg gtc agt gtc cag gct gga aca aag        3834
Lys Gly Ile Tyr Phe Ser Met Val Ser Val Gln Ala Gly Thr Lys
    1265            1270                1275 cgc cag tga                                                         3843
Arg Gln
    1280
```

<210> SEQ ID NO 14
<211> LENGTH: 1280
<212> TYPE: PRT
<213> ORGANISM: Homo Sapiens

<400> SEQUENCE: 14

```
Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Glu Met Thr Asp Ile Phe Ala
65                  70                  75                  80
```

```
Asn Ala Gly Asn Leu Glu Asp Leu Met Ser Asn Ile Thr Asn Arg Ser
             85                  90                  95

Asp Ile Asn Asp Thr Gly Phe Phe Met Asn Leu Glu Glu Asp Met Thr
            100                 105                 110

Arg Tyr Ala Tyr Tyr Ser Gly Ile Gly Ala Gly Val Leu Val Ala
            115                 120                 125

Ala Tyr Ile Gln Val Ser Phe Trp Cys Leu Ala Ala Gly Arg Gln Ile
            130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Phe Thr Gly Phe Ile Val Gly Phe
            195                 200                 205

Thr Arg Gly Trp Lys Leu Thr Leu Val Ile Leu Ala Ile Ser Pro Val
            210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
            245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
            275                 280                 285

Ile Lys Lys Ala Ile Thr Ala Asn Ile Ser Ile Gly Ala Ala Phe Leu
            290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
            325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
            355                 360                 365

Ile Asp Asn Lys Pro Ser Ile Asp Ser Tyr Ser Lys Ser Gly His Lys
            370                 375                 380

Pro Asp Asn Ile Lys Gly Asn Leu Glu Phe Arg Asn Val His Phe Asn
385                 390                 395                 400

Tyr Pro Ser Arg Lys Glu Val Lys Ile Leu Lys Gly Leu Asn Leu Lys
            405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
            435                 440                 445

Gly Met Val Ser Val Asp Gly Gln Asp Ile Arg Thr Ile Asn Val Arg
            450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
            485                 490                 495
```

```
Met Asp Glu Ile Glu Lys Ala Val Lys Glu Ala Asn Ala Tyr Asp Phe
                500                 505                 510
Ile Met Lys Leu Pro His Lys Phe Asp Thr Leu Val Gly Glu Arg Gly
            515                 520                 525
Ala Gln Leu Ser Gly Gln Lys Gln Arg Ile Ala Ile Ala Arg Ala
        530                 535                 540
Leu Val Arg Asn Pro Lys Ile Leu Leu Leu Asp Glu Ala Thr Ser Ala
545                 550                 555                 560
Leu Asp Thr Glu Ser Glu Ala Val Val Gln Val Ala Leu Asp Lys Ala
                565                 570                 575
Arg Lys Gly Arg Thr Thr Ile Val Ile Ala His Arg Leu Ser Thr Val
            580                 585                 590
Arg Asn Ala Asp Val Ile Ala Gly Phe Asp Asp Gly Val Ile Val Glu
        595                 600                 605
Lys Gly Asn His Asp Glu Leu Met Lys Glu Lys Gly Ile Tyr Phe Lys
    610                 615                 620
Leu Val Thr Met Gln Thr Ala Gly Asn Glu Val Glu Leu Glu Asn Ala
625                 630                 635                 640
Ala Asp Glu Ser Lys Ser Glu Ile Asp Ala Leu Glu Met Ser Ser Asn
                645                 650                 655
Asp Ser Arg Ser Ser Leu Ile Arg Lys Arg Ser Thr Arg Arg Ser Val
            660                 665                 670
Arg Gly Ser Gln Ala Gln Asp Arg Lys Leu Ser Thr Lys Glu Ala Leu
        675                 680                 685
Asp Glu Ser Ile Pro Pro Val Ser Phe Trp Arg Ile Met Lys Leu Asn
690                 695                 700
Leu Thr Glu Trp Pro Tyr Phe Val Val Gly Val Phe Cys Ala Ile Ile
705                 710                 715                 720
Asn Gly Gly Leu Gln Pro Ala Phe Ala Ile Ile Phe Ser Lys Ile Ile
                725                 730                 735
Gly Val Phe Thr Arg Ile Asp Asp Pro Glu Thr Lys Arg Gln Asn Ser
            740                 745                 750
Asn Leu Phe Ser Leu Leu Phe Leu Ala Leu Gly Ile Ile Ser Phe Ile
        755                 760                 765
Thr Phe Phe Leu Gln Gly Phe Thr Phe Gly Lys Ala Gly Glu Ile Leu
    770                 775                 780
Thr Lys Arg Leu Arg Tyr Met Val Phe Arg Ser Met Leu Arg Gln Asp
785                 790                 795                 800
Val Ser Trp Phe Asp Asp Pro Lys Asn Thr Thr Gly Ala Leu Thr Thr
                805                 810                 815
Arg Leu Ala Asn Asp Ala Ala Gln Val Lys Gly Ala Ile Gly Ser Arg
            820                 825                 830
Leu Ala Val Ile Thr Gln Asn Ile Ala Asn Leu Gly Thr Gly Ile Ile
        835                 840                 845
Ile Ser Phe Ile Tyr Gly Trp Gln Leu Thr Leu Leu Leu Leu Ala Ile
    850                 855                 860
Val Pro Ile Ile Ala Ile Ala Gly Val Val Glu Met Lys Met Leu Ser
865                 870                 875                 880
Gly Gln Ala Leu Lys Asp Lys Lys Glu Leu Glu Gly Ala Gly Lys Ile
                885                 890                 895
Ala Thr Glu Ala Ile Glu Asn Phe Arg Thr Val Val Ser Leu Thr Gln
            900                 905                 910
```

-continued

Glu Gln Lys Phe Glu His Met Tyr Ala Gln Ser Leu Gln Val Pro Tyr
            915                 920                 925

Arg Asn Ser Leu Arg Lys Ala His Ile Phe Gly Ile Thr Phe Ser Phe
        930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Phe Gly Ala Met Ala Val Gly Gln Val Ser
            980                 985                 990

Ser Phe Ala Pro Asp Tyr Ala Lys Ala Lys Ile Ser Ala Ala His Ile
        995                 1000                1005

Ile Met Ile Ile Glu Lys Thr Pro Leu Ile Asp Ser Tyr Ser Thr
    1010                1015                1020

Glu Gly Leu Met Pro Asn Thr Leu Glu Gly Asn Val Thr Phe Gly
    1025                1030                1035

Glu Val Val Phe Asn Tyr Pro Thr Arg Pro Asp Ile Pro Val Leu
    1040                1045                1050

Gln Gly Leu Ser Leu Glu Val Lys Lys Gly Gln Thr Leu Ala Leu
    1055                1060                1065

Val Gly Ser Ser Gly Cys Gly Lys Ser Thr Val Val Gln Leu Leu
    1070                1075                1080

Glu Arg Phe Tyr Asp Pro Leu Ala Gly Lys Val Leu Leu Asp Gly
    1085                1090                1095

Lys Glu Ile Lys Arg Leu Asn Val Gln Trp Leu Arg Ala His Leu
    1100                1105                1110

Gly Ile Val Ser Gln Glu Pro Ile Leu Phe Asp Cys Ser Ile Ala
    1115                1120                1125

Glu Asn Ile Ala Tyr Gly Asp Asn Ser Arg Val Val Ser Gln Glu
    1130                1135                1140

Glu Ile Val Arg Ala Ala Lys Glu Ala Asn Ile His Ala Phe Ile
    1145                1150                1155

Glu Ser Leu Pro Asn Lys Tyr Ser Thr Lys Val Gly Asp Lys Gly
    1160                1165                1170

Thr Gln Leu Ser Gly Gly Gln Lys Gln Arg Ile Ala Ile Ala Arg
    1175                1180                1185

Ala Leu Val Arg Gln Pro His Ile Leu Leu Leu Asp Glu Ala Thr
    1190                1195                1200

Ser Ala Leu Asp Thr Glu Ser Glu Lys Val Val Gln Glu Ala Leu
    1205                1210                1215

Asp Lys Ala Arg Glu Gly Arg Thr Cys Ile Val Ile Ala His Arg
    1220                1225                1230

Leu Ser Thr Ile Gln Asn Ala Asp Leu Ile Val Val Phe Gln Asn
    1235                1240                1245

Gly Arg Val Lys Glu His Gly Thr His Gln Gln Leu Leu Ala Gln
    1250                1255                1260

Lys Gly Ile Tyr Phe Ser Met Val Ser Val Gln Ala Gly Thr Lys
    1265                1270                1275

Arg Gln
    1280

ABCB1 GENOTYPING TO PREDICT MICROTUBULE-STABILIZING-AGENT-INDUCED TOXICITY

CROSS-REFERENCE TO RELATED APPLICATION

This is the U.S. Stage of International Application No. PCT/US2007/073497, filed Jul. 13, 2007 (published in English under PCT Article 21(2)), which claims the benefit of U.S. Provisional Application No. 60/807,453 filed Jul. 14, 2006, herein incorporated by reference.

FIELD

This application relates to methods of identifying subjects who are likely to have significant adverse effects from administration of taxanes or other microtubule-stabilizing agents, as well as isolated nucleic acid molecules and kits that can be used to practice these methods.

BACKGROUND

Taxanes are a family of compounds that were originally identified in extracts of the bark of the yew tree (*Taxus*). Paclitaxel (Taxol®) and docetaxel (Taxotere®) are taxanes with broad antitumor activity. These drugs were originally approved for use in breast or ovarian tumor subjects, but they have activity against diverse tumors including lymphoma, non-small-cell lung, head and neck, gastric, bladder, prostate, and other carcinomas. Dosing and scheduling of these drugs have been optimized throughout the last two decades. Adverse effects caused by taxane treatment include severe hypersensitivity reaction, neutropenia, peripheral neuropathy, myalgia/arthralgia, skin and nail disorders, and alopecia. Neutropenia is the major dose-limiting toxicity of treatment with paclitaxel, while the frequency of peripheral neuropathy appears to increase with cumulative dose. Although the incidence of severe hypersensitivity reactions has been reduced by the use of premedication, cumulative peripheral neuropathy and neutropenia persist as challenges to optimal treatment with taxanes.

Taxanes are part of the larger family of anti-cancer drugs whose mechanism of action targets microtubules (MTs). Both paclitaxel and docataxel bind to the f3-tubulin subunit and stabilize MTs. This stabilization of the MTs leads to mitotic arrest and subsequent apoptosis. Other compounds with a similar mechanism of action include the epothilones, discodermolide, eleutherobin, the sarcodictyins, and the laulimalides (He et al., (2001) *Drug Discovery Today* 6:1153-1164).

One of the primary proteins involved in taxane elimination and distribution is ABCB1 (also known as multi-drug resistance 1 (MDR1) or P-glycoprotein). ABCB1 is a member of the ATP-binding cassette family of efflux transporters that are expressed in several tissues, including tissues with excretory function, neural stem cells, the blood-brain-barrier, and hematopoietic precursor cells. Although ABCB1 has not been detected in peripheral nerve cells, the transfer of drugs across the systemic circulation to the peripheral nerves is regulated by the blood-nerve barrier consisting of capillary endothelial cells. The cells that make up the blood-nerve barrier express ABCB1 and are thought to protect the peripheral nervous tissue by transporting toxic substances from the nervous system back into the systemic circulation.

Due to the severity of adverse effects resulting from administration of taxanes and other MT-stabilizing agents, methods for identifying individuals at increased risk for these side effects prior to commencement of treatment are needed.

SUMMARY

Polymorphisms in the ABCB1 gene have been identified that are predictive for adverse effects induced by treatment with taxanes or other microtubule (MT)-stabilizing agents. Based on these observations, methods are provided for identifying a subject at increased risk for adverse effects. In some examples, subjects identified as having an increased risk of adverse MT-stabilizing agent side effects receive a modified therapy designed to reduce such undesirable side effects.

In one example, the method includes determining the subject's genotype for ABCB1 predictive polymorphisms, such as those that indicate an increased likelihood of a particular clinical outcome. Exemplary ABCB1 predictive polymorphisms include, but are not limited to, one or more of 1236C>T, 2677G>T/A, and 3435C>T, such as two, three or four of such polymorphisms (for example 2677G>T/A and 3435C>T). In particular examples, the presence of one or more of these polymorphisms, such as two or three of these polymorphisms, is predictive of increased risk for adverse effects, while the absence of such predictive polymorphisms indicates that the subject will not likely experience adverse effects. In a particular example, the MT-stabilizing agent is a taxane. In another particular example, the MT-stabilizing agent is an epothilone.

Methods are also provided to decrease the occurrence of MT-stabilizing-agent-induced adverse effects by determining the genotype of a subject for ABCB1 polymorphisms and altering the course of treatment if the subject has at least one predictive polymorphism, such as at least two or at least three of such predictive polymorphisms. In one example, the amount of MT-stabilizing agent administered to a subject is decreased, for example wherein the dosage is decreased by at least 20%. In another example, the interval between treatments with MT-stabilizing agent is increased or the duration of MT-stabilizing agent infusion is increased (for example administering the same dose of a MT-stabilizing agent over a greater period of time). In yet another example, a therapeutically effective amount of colony-stimulating factor (CSF) is administered following MT-stabilizing agent treatment in order to reduce the incidence of neutropenia. Combinations of these can also be used.

Also provided are isolated nucleic acid molecules, such as those that consist of any of SEQ ID NOs: 1-12. One skilled in the art will appreciate that such primers can include a detectable label, such as a fluorophore or enzyme. Kits are disclosed that can be used to identify a subject at increased risk for MT-stabilizing-agent-induced adverse effects. In one example, two or more primers shown in SEQ ID NOs: 1-12 are included in the kit, for example to detect the presence or absence of one or more predictive polymorphisms in the ABCB1 gene. Such kits can include additional reagents, such as buffers and reagents that permit detection of a nucleic acid molecule, for example by amplification and/or specific hybridization.

The foregoing and other objects and features of the disclosure will become more apparent from the following detailed description, which proceeds with reference to the accompanying figures.

Figure 2:
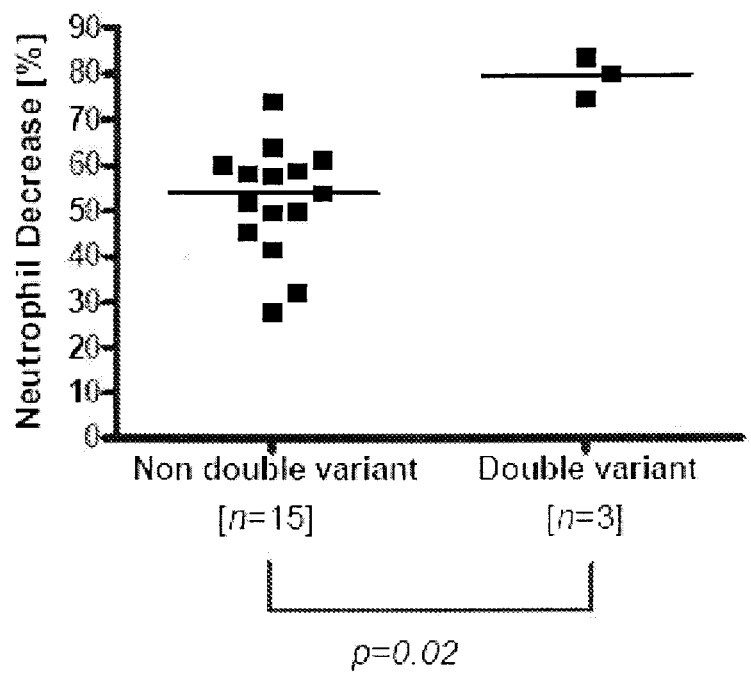

FIG. 2 is a diagram showing the association between the risk of neutropenia and ABCB1 genotype status in 18 subjects. Data are presented as a percentage decrease in absolute neutrophil count for each genotype following 12 weeks of paclitaxel treatment. Non-double variant, wild type at both, or heterozygous at one or both of ABCB1 2677 and ABCB1 3435 alleles; double variant, ABCB1 2677TT and ABCB1 3435TT genotype. The unadjusted P value was 0.0025.

Figure 3:
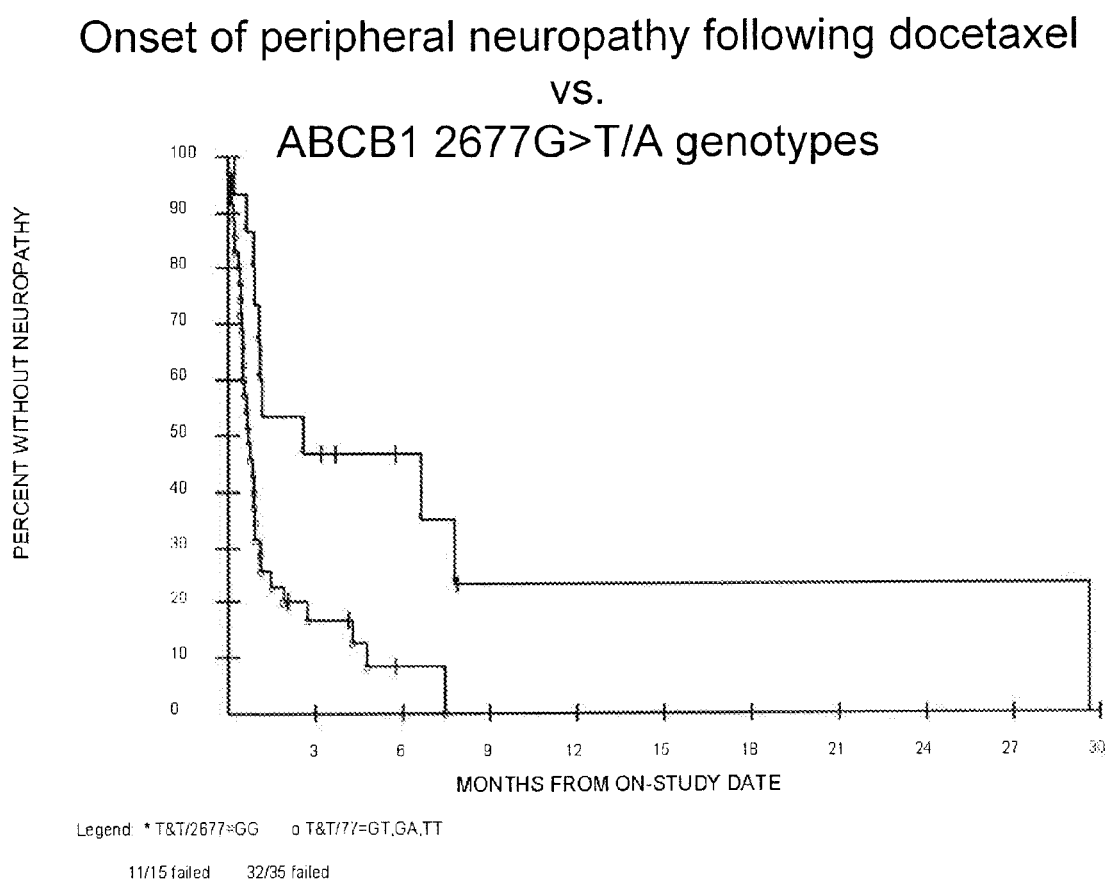

FIG. 3 is a diagram showing the association between onset of docetaxel-induced peripheral neuropathy and ABCB1 genotype status in 50 subjects receiving docetaxel once a week for 3 consecutive weeks followed by a 1 week rest period until treatment failure. Data are presented as a percentage decrease of subjects having no neuropathy for each genotype. Upper trace shows subjects having the ABCB1 2677GG genotype (wild-type a both alleles), lower trace shows subjects having the ABCB1 2677GT or 2677GA (heterozygous at the ABCB1 2677 allele) or the double variant ABCB1 2677TT genotype. The P value was 0.017 by Log-Rank Test.

SEQUENCE LISTING

The nucleic acid sequences listed in the accompanying sequence listing are shown using standard letter abbreviations for nucleotide bases, as defined in 37 C.F.R. 1.822. Only one strand of each nucleic acid sequence is shown, but the complementary strand is understood as included by any reference to the displayed strand. In the accompanying sequence listing:

SEQ ID NO: 1 and SEQ ID NO: 2 are forward and reverse primers, respectively, used to PCR amplify ABCB1 to detect polymorphisms at nucleotide 1236.

SEQ ID NO: 3 and SEQ ID NO: 4 are forward and reverse primers, respectively, used to PCR amplify ABCB1 to detect polymorphisms at nucleotide 2677.

SEQ ID NO: 5 and SEQ ID NO: 6 are forward and reverse primers, respectively, used to PCR amplify ABCB1 to detect polymorphisms at nucleotide 3435.

SEQ ID NO: 7 and SEQ ID NO: 8 are forward and reverse primers, respectively, used to sequence PCR products encompassing ABCB1 position 1236 in order to determine genotype.

SEQ ID NO: 9 and SEQ ID NO: 10 are forward and reverse primers, respectively, used to sequence PCR products encompassing ABCB1 position 2677 in order to determine genotype.

SEQ ID NO: 11 and SEQ ID NO: 12 are forward and reverse primers, respectively, used to sequence PCR products encompassing ABCB1 position 3435 in order to determine genotype.

SEQ ID NO: 13 is an exemplary human ABCB1 cDNA sequence that can be used to identify the referenced 1236, 2677, and 3435 positions disclosed herein.

SEQ ID NO: 14 is the protein encoded by SEQ ID NO: 13.

DETAILED DESCRIPTION

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "including a nucleic acid" includes single or plural nucleic acids and is considered equivalent to the phrase "including at least one nucleic acid." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. For example, the phrase "mutations or polymorphisms" or "one or more mutations or polymorphisms" means a mutation, a polymorphism, or combinations thereof, wherein "a" can refer to more than one.

Although methods and materials similar or equivalent to those described herein can be used in the practice or testing of the present disclosure, suitable methods and materials are described below. The materials, methods, and examples are illustrative only and not intended to be limiting.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

ABCB1: ATP-binding cassette, sub-family B (MDR/TAP), member 1 gene or protein
CSF: colony-stimulating factor
G-CSF: granulocyte colony-stimulating factor
GM-CSF: granulocyte macrophage colony-stimulating factor
MDR1: multi-drug resistance gene or protein
MT: microtubule
PCR: polymerase chain reaction ABCB1: ATP-binding cassette, sub-family B (MDR/TAP), member 1; otherwise known as the multidrug resistance gene (MDR1), encoding the protein known as P-glycoprotein. ABCB1 is a member of the ATP-binding cassette family of efflux transporters. It was first discovered as a protein responsible for resistance against anti-cancer drugs in human cancer cells. In general, ABCB1 is expressed in many normal tissues, for example, intestinal epithelium, adrenal gland, kidney, liver, pancreas, and capillary endothelial cells of the brain and testes. It plays a role in excretion of foreign xenobiotics from the body and preventing their transfer across the placenta and the blood-brain barrier.

ABCB1 sequences are publicly available. For example, GenBank Accession number NC 000007 discloses a human ABCB1 gene sequence, and GenBank Accession numbers BC130424 and AY910577 disclose exemplary human ABCB1 cDNA sequences and AAI30425 and AAW82430 disclose exemplary human ABCB1 protein sequences. One skilled in the art will appreciate that ABCB1 nucleic acid and protein molecules can vary from those publicly available, such as ABCB1 sequences having one or more substitutions, deletions, insertions, or combinations thereof, while still retaining ABCB1 biological activity. In addition, ABCB1 molecules include fragments that retain the desired ABCB1 biological activity.

Administration: To provide or give a subject an agent, such as a composition that includes a MT-stabilizing agent, such as a taxane or an epothilone, alone or in combination with another agent, by any effective route. Exemplary routes of administration include, but are not limited to, oral, injection (such as subcutaneous, intramuscular, intradermal, intraperitoneal, and intravenous), sublingual, rectal, transdermal, intranasal, vaginal and inhalation routes.

Analog: A synthetic chemical compound using a common structure as a backbone (for example, where side groups have been added or such groups have been deleted from the parent structure). The analog differs in structure from the parent molecule such as by a difference in the length of an alkyl chain, a molecular fragment, by one or more functional groups, or a change in ionization. For example, an analog of paclitaxel will have the taxane ring structure (as described by Kinston et al., *Progress in the Chemistry of Organic Natural Products*, Springer-Verlag, 1993) with alterations in side chains as compared with paclitaxel.

Cancer: Malignant neoplasm that has undergone characteristic anaplasia with loss of differentiation, increased rate of growth, invasion of surrounding tissue, and is capable of metastasis.

Colony-stimulating factor (CSF): Any of a family of glycoproteins which promote the differentiation of hematopoietic stem cells, particularly to neutrophils or macrophages. In one particular example, a CSF is granulocyte colony-stimulating factor (G-CSF). In another example, a CSF is granulocyte macrophage colony-stimulating factor (GM-CSF). In some examples, therapeutically effective amounts of CSF can be used to treat neutropenia.

Decreased/decreasing: Becoming less or smaller, as in number, amount, or intensity. In one example, reducing the frequency of occurrence of MT-stabilizing-agent-induced adverse effects by at least 10%, at least 20%, at least 30%, or at least 50%. In another example, reducing the amount of MT-stabilizing agent administered to a subject by at least 10%, at least 20%, at least 30%, or at least 50%. In a further example, reducing the incidence, duration, or severity of adverse effects induced by MT-stabilizing agents.

Docetaxel (Taxotere®): A member of the taxane family of compounds with anti-tumor activity derived from *Taxus baccata* by a semi-synthetic process, with the chemical formula (2R,3S)—N-carboxy-3-phenylisoserine,N-tert-butyl ester, 13-ester with 5β-20-epoxy-1,2α,4,7β,10β,13α-hexahydroxytax-11-en-9-one 4-acetate 2-benzoate, trihydrate. Docetaxel is an anti-microtubule agent that promotes the assembly and stabilization of MTs by preventing depolymerization. Stabilization of MTs leads to mitotic arrest and cytotoxicity.

Dosing schedule: Timing of administration of a therapeutic agent, such as a MT-stabilizing agent. For example, a therapeutic agent can be administered at least one time per day, at least once per week, at least once every two weeks, at least once every three weeks, or at least once every six weeks. In a specific example, paclitaxel dosing schedule can be a three hour infusion once ever three weeks.

Epothilone: A class of microlides initially discovered from the myxobacterium *Sorangium cellulosum*. Epothilones have MT-stabilizing activity and may have antitumor activity. Examples include epothilone A, epothilone B, and ixabepilone.

Granulocyte colony-stimulating factor (G-CSF): A member of the family of CSFs which stimulates growth and differentiation of neutrophils from the hematopoietic precursor cell population. G-CSF can be used as an adjunct to cytotoxic chemotherapy treatment of solid tumors. It has been shown to reduce incidence of febrile neutropenia and decrease time of recovery of neutrophil levels following chemotherapy. A pegylated form of G-CSF has also been approved for use in treating neutropenia. See Komrokji and Lyman (2004) *Expert Opin. Biol. Ther.* 4:1897-1910.

Granulocyte macrophage colony-stimulating factor (GM-CSF): A member of the family of CSFs which stimulates proliferation of neutrophils, macrophages, and eosinophils. GM-CSF can be used to treat neutropenia that occurs as a result of cytotoxic chemotherapy for solid tumors. See Komrokji and Lyman (2004) *Expert Opin. Biol. Ther.* 4:1897-1910.

Increased: Greater in amount, size, or degree. In one example, the time period during which MT-stabilizing agent chemotherapy is administered is lengthened by at least two hours, such as at least 23 hours. In another example, the interval between administration of doses of MT-stabilizing agent is lengthened by at least one week, at least two weeks, or at least five weeks.

Increased risk: An elevated likelihood that a certain event will occur. For example, subjects having one or more predictive polymorphisms in the ABCB1 gene may have an increased probability of experiencing MT-stabilizing-agent-induced adverse effects, such as neutropenia or peripheral neuropathy.

Isolated: An "isolated" biological component (such as a nucleic acid molecule, protein, or cell) has been substantially separated or purified away from other components, such as other components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules (such as DNA or RNA) and proteins purified by standard purification methods. The term also embraces nucleic acid molecules and proteins prepared by recombinant expression in a host cell as well as chemically synthesized nucleic acid molecules and proteins.

Ixabepilone (BMS-247550): A member of the family of epothilones with the chemical structure (1S,3S,7S,10R,11S,12S,16R)-7,11-dihydroxy-8,8,10,12,16-pentamethyl-3-[(1E)-1-methyl-2-(2-methylthiazol-4-yl)ethenyl]-17-oxa-4-azabicyclo[14.1.0]heptadecane-5,9-dione.

Microtubule-stabilizing agent: A class of compounds that bind to tubulin oligomers or polymers and enhances polymerization of tubulin or stabilizes MTs. This is in contrast to agents that depolymerize MTs, such as the vinca alkaloids. In one example, a MT-stabilizing agent is a taxane, such as paclitaxel. In another example, a MT-stabilizing agent is an epothilone, such as ixabepilone. In a further example, a MT-stabilizing agent is discodermolide or eleutherobin. In another example, a MT-stabilizing agent is a sarcodictyins or a laulimalide.

Microtubule-stabilizing-agent-induced adverse effects: Negative side effects resulting from administration of a MT-stabilizing agent anti-cancer drug to a subject, such as a human. Exemplary effects include hypersensitivity reaction, hematological effects (neutropenia, leucopenia, anemia), cardiovascular effects (bradycardia, hypotension), peripheral neuropathy, myalgia/arthralgia, nausea and vomiting, alopecia, and combinations thereof. Other effects are known to skilled clinicians.

Neutropenia: A condition wherein there is a reduction in the blood neutrophil count, often leading to increased susceptibility to infection. The severity of neutropenia is generally defined by the absolute neutrophil count—mild, between $1 \times 10^9$/ml and $2 \times 10^9$/ml; moderate, between $0.5 \times 10^9$/ml and $1 \times 10^9$/ml; severe, less than $0.5 \times 10^9$/ml. The most common cause of neutropenia is impaired neutrophil production as a result of drug treatment, particularly anti-cancer drugs. In one example, MT-stabilizing-agent-induced neutropenia may be treated by adjusting MT-stabilizing agent treatment or by administering CSFs subsequent to MT-stabilizing agent treatment.

Paclitaxel (Taxol®) A member of the taxane family with anti-tumor activity derived from *Taxus baccata* by a semi-synthetic process, with the chemical formula 5β,20-Epoxy-1,2α,4,7β,10β,13α-hexahydroxytax-11-en-9-one 4,10-diacetate 2-benzoate 13-ester with (2R,3S)—N-benzoyl-3-phenylisoserine. Paclitaxel is an anti-microtubule agent that promotes the assembly and stabilization of MTs by preventing depolymerization. Stabilization of MTs leads to mitotic arrest and cytotoxicity. Paclitaxel treatment generally results in lower rates of neutropenia than docetaxel treatment.

Peripheral neuropathy: A syndrome of sensory loss, muscle weakness and atrophy, decreased deep tendon reflexes, and vasomotor symptoms, singly or in any combination. In one example, MT-stabilizing agent-induced peripheral neuropathy is most commonly characterized by numbness and parathesia in a glove-and-stocking distribution. In a further example, MT-stabilizing-agent-induced peripheral neuropathy may be treated by adjusting MT-stabilizing agent treatment.

Polymorphism: A variation in a gene sequence, such as a variation in an ABCB1 sequence. The polymorphisms can be those variations (DNA sequence differences) which are generally found between individuals or different ethnic groups and geographic locations which, while having a different sequence, produce functionally equivalent gene products. The term can also refer to variants in the sequence which can lead to gene products that are not functionally equivalent. Polymorphisms also encompass variations which can be classified as alleles and/or mutations which can produce gene products which may have an altered function. Polymorphisms also encompass variations which can be classified as alleles and/or mutations which either produce no gene product or an inactive gene product or an active gene product produced at an abnormal rate or in an inappropriate tissue or in response to an inappropriate stimulus. Further, the term is also used interchangeably with allele as appropriate.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation. For example, a 1236C>T polymorphism in ABCB1 refers to a substitution of the C at position 1236 of the ABCB1 cDNA sequence for a T, which does not result in any amino acid change in the protein. In another example, a 2677G>T/A polymorphism refers to a substitution of the G at position 2677 of the ABCB1 cDNA sequence for a T or an A, resulting in a change of alanine 893 in the protein to serine or threonine, respectively. In a further example, 3435C>T refers to a substitution of the C at position 3435 of the ABCB1 cDNA sequence for a T, which does not result in any amino acid change in the protein. The locations of these positions can be determined from an ABCB1 cDNA sequence known in the art, for example GenBank Accession No. BC130424 (SEQ ID NO: 13).

A predictive polymorphism is one that indicates an increased likelihood of a particular clinical outcome. For example, the presence of one of more of the 1236C>T, 2677G>T/A, and 3435C>T polymorphisms in the ABCB1 gene are indicative of a subject more likely to experience adverse effects from MT-stabilizing agent treatment (such as peripheral neuropathy or neutropenia) as compared to a subject not having these polymorphisms.

Sample: Includes biological samples that contain cells, genomic DNA, RNA, or proteins (or combinations thereof) obtained from a subject, such as those present in peripheral blood, urine, saliva, sputum, tissue biopsy, surgical specimen, fine needle aspirate, and autopsy material. In a particular example, a sample includes blood plasma obtained from a human subject.

Subject: Living multi-cellular vertebrate organisms, a category that includes human and non-human mammals (such as laboratory or veterinary subjects).

Subsequent to: At a time later than or after another event. For example, subsequent administration of a CSF indicates administration of a CSF at some time following administration of a MT-stabilizing agent, such as at least 24 hours after MT-stabilizing agent administration, at least 72 hours after MT-stabilizing agent administration, or at least seven days following MT-stabilizing agent administration.

Synonymous substitution: A nucleotide substitution that results in a new codon specifying the same amino acid. Such substitutions often occur at the third base position of a codon. However, base substitution at the first base position can occasionally give rise to a synonymous substitution, as in the case of some leucine and arginine codons (for example CUA⇔UUA, CUG⇔UUG, AGA⇔CGA and AGG⇔CGG).

Taxane: A "taxane" is a chemical based on the taxane ring structure as described in Kinston et al., *Progress in the Chemistry of Organic Natural Products*, Springer-Verlag, 1993. A member of the group of complex diterpenoids derived from the bark of *Taxus brevifolia* or semi-synthetically from the needles of a member of the genus *Taxus*, such as *Taxus baccata*. Taxanes may also be made synthetically by total synthesis. Their mechanism of action is through binding to tubulin polymers and stabilizing the MT, resulting in cell cycle arrest and ultimately cell death. Taxanes can be used as antineoplastic agents in the treatment of a number of solid tumors, including breast, ovary, non-small cell lung, and prostate. In one example, a taxane is paclitaxel. In another example, a taxane is docetaxel. In a further example, a taxane is an analog of paclitaxel containing the taxane ring structure.

Therapeutically effective amount: An amount of a therapeutic agent (such as a composition that includes a MT-stabilizing agent, such as paclitaxel or ixabepilone), that alone, or together with one or more additional therapeutic agents, induces the desired response, such as treatment of a solid tumor, such as breast, ovarian, non-small cell lung, or AIDS-related Kaposi's sarcoma. In one example, it is an amount of MT-stabilizing agent needed to prevent or delay the development of a tumor, prevent or delay the metastasis of a tumor, cause regression of an existing tumor, or treat one or more signs or symptoms associated with a tumor, in a subject, such as a subject having breast cancer. Ideally, a therapeutically effective amount provides a therapeutic effect without causing a substantial cytotoxic effect in the subject. The preparations disclosed herein are administered in therapeutically effective amounts.

In one example, a desired response is to decrease the size, volume, or number (such as metastases) of a solid tumor. For example, the composition that includes a MT-stabilizing agent can in some examples decrease the size, volume, or number of tumors (such as ovarian tumors) by a desired amount, for example by at least 5%, at least 10%, at least 15%, at least 20%, at least 25%, at least 30%, at least 50%, at least 75%, or even at least 90%, as compared to a response in the absence of the therapeutic composition.

In general, an effective amount of a composition that includes a MT-stabilizing agent administered to a human subject will vary depending upon a number of factors associated with that subject, for example the overall health of the subject. An effective amount of a composition that includes a MT-stabilizing agent can be determined by varying the dosage of the product and measuring the resulting therapeutic response, such as the regression of a tumor. The disclosed therapeutic agents can be administered in a single dose, or in several doses, as needed to obtain the desired response. However, the effective amount can be dependent on the source applied, the subject being treated, the severity and type of the condition being treated, and the manner of administration.

In particular examples, a therapeutically effective dose of a MT-stabilizing agent includes at least 35 mg/m² (such as 35-300 mg/m²) of paclitaxel administered intravenously over at least 1 hour (such as 1-24 hours) at least every one week (such as every 1-3 weeks). The disclosed compositions that include a MT-stabilizing agent can be administered alone, in the presence of a pharmaceutically acceptable carrier, in the presence of other therapeutic agents (such as other anti-neoplastic agents), or both.

Treatment: Refers to a therapeutic intervention that ameliorates a sign or symptom of a disease or pathological condition related to a disease (such as a tumor, for example a breast, ovarian, or lung tumor). Treatment can also induce remission or cure of a condition, such as a tumor. Reducing a sign or symptom associated with a tumor (such as a breast, ovarian, or lung tumor) can be evidenced, for example, by a delayed onset of clinical symptoms of the disease, a reduction in severity of some or all clinical symptoms of the disease, a slower progression of the disease (for example by prolonging the life of a subject having tumor), a reduction in the number of relapses of the disease, an improvement in the overall health or well-being of the subject, or by other parameters well known in the art that are specific to the particular tumor. In another example, treatment can include a therapeutic intervention that ameliorates a MT-stabilizing agent-induced adverse effect, such as peripheral neuropathy or neutropenia, for example by altering the MT-stabilizing agent treatment regimen.

Treatment includes preventing a disease, for example by inhibiting the full development of a disease, such as preventing development of a tumor (such as a metastasis or the development of a primary tumor). Prevention does not require a total absence of a tumor. In one example, treatment includes therapeutic intervention that prevents the development of MT-stabilizing-agent-induced adverse effects such as peripheral neuropathy or neutropenia. In a particular example, if a subject is determined to have an ABCB1 polymorphism predictive for MT-stabilizing-agent-induced neutropenia, treatment can include administration of a CSF to prevent development of neutropenia.

Tumor: A neoplasm. A particular type of tumor is a solid tumor. Examples of solid tumors, such as sarcomas and carcinomas, include, but are not limited to: fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). Certain classes of tumors respond therapeutically to treatment with a MT-stabilizing agent and this class of tumors is referred to as an MT-stabilizing agent responsive tumor.

Methods of Identifying Risk for Adverse Effects

Methods are provided for identifying a subject at increased risk for developing MT-stabilizing-agent-induced adverse effects. The subject may, for example, have a tumor that is believed to be a tumor that is responsive to a MT-stabilizing agent. In one example, the method includes determining whether the subject has at least one predictive polymorphism in an ABCB1 gene, wherein the presence of at least one predictive polymorphism in an ABCB1 gene (such as at least two predictive polymorphisms in an ABCB1 gene) indicates that the subject has an increased risk for developing MT-stabilizing-agent-induced adverse effects. In contrast, a subject not having a predictive polymorphism in an ABCB1 gene indicates that the subject does not have an increased risk for MT-stabilizing-agent-induced adverse effects.

A predictive polymorphism is one that indicates that a subject has an increased likelihood of a particular clinical outcome. For example, an ABCB1 predictive polymorphism includes one or more ABCB1 polymorphisms that can be used to determine whether a subject has an increased likelihood of developing one or more adverse effects resulting from treatment with a MT-stabilizing agent. Particular examples of predictive ABCB1 polymorphisms include, but are not limited to: 1236C>T, 2677G>T, 2677G>A, or 3435C>T, or combinations thereof.

In one example, if the subject has at least two or at least three predictive polymorphisms in an ABCB1 gene, this indicates that the subject is at increased risk for developing MT-stabilizing-agent-induced adverse effects, such as peripheral neuropathy and neutropenia. For example, if the subject has an ABCB1 3435C>T polymorphism, this can indicate an increased risk for development of peripheral neuropathy following administration of a MT-stabilizing agent. In another example, if the subject has both 2677G>T/A and 3435C>T ABCB1 polymorphisms, the subject can have an increased risk for development of neutropenia following MT-stabilizing agent treatment.

Determining ABCB1 Genotype

Nucleic acids suitable for detecting polymorphisms in ABCB1 can be obtained from numerous biological sources. Exemplary biological samples include, but are not limited to, whole blood or fractions thereof (such as plasma), buccal cells obtained by swab or mouthwash, tumor biopsy, fine needle aspirates, amniocentesis or chorionic villus samples, pathological samples, and blood spots on Guthrie cards. See, for example, Chapter 17 in *Human Molecular Genetics* 2. Eds. Tom Strachan and Andrew Read. New York: John Wiley & Sons Inc., 1999. In one example, DNA is isolated from plasma from a subject.

Methods to isolate nucleic acids (such as genomic DNA, cDNA, or mRNA) from a biological sample are known in the art. Although exemplary methods are provided, the methods are not limited to those listed. Particular methods of isolating nucleic acid molecules from a biological sample are well known in the art, and can include ethanol precipitation following cell lysis, column purification methods, and magnetic or glass bead-based isolation methods. In addition, commercially available kits can be used, such as QIAamp® DNA purification kits (Qiagen, Valencia, Calif.) or PUREGENE® DNA purification kits (Gentra Systems, Minneapolis, Minn.). In a particular example, genomic DNA is isolated from human plasma from a subject using a spin column method.

Methods for detecting polymorphisms (such as predictive polymorphism of ABCB1) in a nucleic acid molecule are known in the art. Although exemplary methods are provided, the methods are not so limited. Particular methods of detecting a predictive polymorphism at one or more particular nucleotides (for example in ABCB1) include, but are not limited to, restriction fragment length polymorphism (RFLP), single strand conformational polymorphism (SSCP) mapping, direct nucleic acid sequencing, hybridization, fluorescent in situ hybridization (FISH), pulsed field gel electrophoresis (PFGE) analysis, RNase protection assay, allele-specific oligonucleotide (ASO), dot blot analysis, allele-specific PCR amplification (ARMS), oligonucleotide ligation assay (OLA) and PCR-SSCP. Methods of performing such methods are routine. See, for example, Chapters 6 and 17 in *Human Molecular Genetics* 2. Eds. Tom Strachan and Andrew Read. New York: John Wiley & Sons Inc., 1999.

In a particular example, the presence of one or more predictive polymorphisms, such as those of ABCB1, is determined by direct nucleotide sequencing. In a further example, the presence of one or more polymorphisms is determined by a Taq polymerase assay, such as a TaqMan® assay (Holland et al. (1991) *Proc. Natl. Acad. Sci. U.S.A.* 88:7276-80; Lee et al. (1999) *J. Mol. Biol.* 285:73-83). This assay is based on the fact that Taq polymerase does not possess a proofreading 3' to 5' exonuclease activity, but possesses a 5' to 3' exonuclease activity. This assay involves the use of two conventional PCR primers (forward and reverse), which are specific for the target sequence (such as ABCB1), and a third primer, which is allele-specific, designed to bind specifically to a site on the target sequence downstream of the forward primer binding site. The third primer is generally labeled with two fluorophores, a reporter dye at the 5' end, and a quencher dye, having a different emission wavelength compared to the reporter dye, at the 3' end. The third primer also carries a blocking group at the 3' terminal nucleotide, so that it cannot by itself prime any new DNA synthesis. During the PCR reaction, Taq DNA polymerase synthesizes a new DNA strand primed by the forward primer and as the enzyme approaches the third primer, its 5' to 3' exonuclease activity processively degrades the third primer from its 5' end. The end result is that the nascent DNA strand extends beyond the third primer binding site and the reporter and quencher dyes are no longer bound to the same molecule. As the reporter dye is no longer near the quencher dye, the resulting increase in reporter emission intensity can be detected.

In another example, the presence of predictive polymorphisms in ABCB1 can be detected using an oligonucleotide ligation assay (OLA) method. The OLA includes two phases, a PCR amplification and an oligonucleotide ligation. In the first reaction a PCR primer is hybridized to the target sequence. The primers are designed with either the normal or mutant nucleotide(s) at the 3' end and differing fluorescent labels at the 5' end. The second reaction is a ligation reaction. A common primer which is complementary to the target DNA sequence immediately downstream (3') of the SNP site is ligated to a primer which perfectly matches the 5' sequence. The resulting ligated oligonucleotide products can be detected using capillary gel electrophoresis and fluorescent detection of the respective fluorescent tags in order to determine genotype.

In a further example, a bead-based assay utilizing hybridization of allele-specific oligonucleotides attached to a fluorescent label can be used to identify polymorphisms in ABCB1. Oligonucleotides specific to each allele, which are attached to different fluorescently labeled beads, are hybridized to amplified DNA containing the polymorphism of interest. The allele-specific oligonucleotides will only significantly hybridize if the allele is present in the sample. The hybridized beads are then captured, for example with a biotinylated detector molecule, and the relative fluorescence of the beads for each label is measured. This allows the determination of genotype for a particular polymorphism, for example in the ABCB1 gene.

Subjects

In one example, mammalian subjects are analyzed for the presence of one or more ABCB1 predictive polymorphisms, such as a human or veterinary subject. In some examples, the subject has a disorder that can be treated by administration of a MT-stabilizing agent. Examples of disorders that can be treated by administration of a MT-stabilizing agent include, but are not limited to, solid tumors, such as solid cancers of the breast, lung (such as non-small cell lung carcinoma), ovary, bladder or ureter, esophagus, head or neck, and kidney, as well as Kaposi's sarcoma.

For example, the subject can be receiving treatment for a tumor which includes administration of a MT-stabilizing agent. In another example, the subject is a candidate for administration of a MT-stabilizing agent, for example, someone who has a tumor of the MT-stabilizing agent responsive type.

Microtubule-Stabilizing Agents

Particular ABCB1 polymorphisms are associated with increased risk of occurrence of adverse effects following administration of MT-stabilizing agents, and are referred to herein as predictive ABCB1 polymorphisms. MT-stabilizing agents are compounds that bind to tubulin oligomers or polymers and enhance polymerization of tubulin or stabilize MTs, leading to cytotoxicity.

In one example, the MT-stabilizing agent is from the class of epothilones, such as ixabepilone (BMS-247550). In another example, the MT-stabilizing agent is from the class of taxanes, such as paclitaxel (Taxol®), docetaxel (Taxotere®), or a chemical analog of paclitaxel that shares the taxane ring backbone.

Adverse Effects

It is shown herein that particular polymorphisms in an ABCB1 gene are associated with increased risk for certain adverse effects induced by MT-stabilizing agents. MT-stabilizing-agent-induced adverse effects include undesirable side effects that can result from the administration of therapeutically effective amounts of a MT-stabilizing-agent. In some examples, such effects are not observed uniformly throughout a population. That is, some subjects suffer more effects or more severe effects than others. In particular examples, the disclosed methods can be used to distinguish such subjects.

In one example, the adverse effect is peripheral neuropathy. In a particular example, increased risk of developing peripheral neuropathy is predicted by the presence of the polymorphism 3435C>T. In another example, the adverse effect is neutropenia. In a particular example, increased risk of developing neutropenia is predicted by the presence of polymorphisms at both 2677G>T/A and 3435C>T.

Method for Decreasing Occurrence of Adverse Effects

Methods are provided for decreasing the occurrence of one or more MT-stabilizing-agent adverse effects, such as peripheral neuropathy and neutropenia. In one example, the genotype of a subject for ABCB1 predictive polymorphisms 2677G>T/A and 3435C>T is determined, and if the subject is determined to have at least one predictive polymorphism, thus indicating that the subject has an increased risk of developing one or more MT-stabilizing-agent adverse effects, approaches can be taken to reduce the MT-stabilizing-agent adverse effects.

For example, administration of a MT-stabilizing agent can be modified, agents can be administered that are known to treat one or more MT-stabilizing-agent adverse effects, or combinations thereof, thereby decreasing the occurrence of adverse effects in the subject having an increased risk of developing MT-stabilizing-agent adverse effects.

Microtubule-Stabilizing Agent Administration

The amount, timing, or rate of administration (or combinations thereof) of a MT-stabilizing agent can be modified to reduce the occurrence or severity of adverse effects caused by the treatment, such as peripheral neuropathy and neutropenia. In some examples the modifications are relative to routine therapeutic methods for administering an MT-stabilizing agent to a subject (such as what would be routine for a cancer patient). In one example, the amount of MT-stabilizing agent administered is decreased, for example relative to an amount routinely administered, such as a reduction of at least 10%, at least 20%, at least 30%, or at least 50%. In a particular example, the dose of paclitaxel is reduced from 175 mg/m$^2$ to an amount less than 175 mg/m$^2$ (such as 150 mg/m$^2$ to 50 mg/m$^2$, such as 140 mg/m$^2$ to 100 mg/m$^2$, for example 135 mg/m$^2$). In another example, the interval between administration of doses of a MT-stabilizing agent is increased, for example relative to an interval routinely used. In particular examples the interval is increased by at least one week, at least two weeks, or at least five weeks. In a further example, the interval between doses of microtubule-stabilizing agent is increased from one week to three weeks. In another example, the rate of administration of the MT-stabilizing agent is decreased by increasing the time period of administration, for example relative to a rate routinely administered. In particular examples the time of administration is increased by at least one hour, at least two hours, or at least 23 hours. In a further example, the time of administration is increased from one hour to three hours.

Administration of Additional Treatments

Neutropenia

The incidence, severity, or duration of neutropenia in subjects identified to be at increased risk based on ABCB1 genotype can be reduced by additional treatment. In one example, a therapeutically effective amount of CSF is administered to subjects at risk for MT-stabilizing agent-induced neutropenia, for example before, during, or after administration of the MT-stabilizing agent. In a particular example, a therapeutically effective amount of CSF is administered subsequent to MT-stabilizing agent administration. In a particular example, the CSF is G-CSF. In a further example, at least 1 µg/kg/day of G-CSF (such as 4-8 µg/kg/day of G-CSF, for example 5 µg/kg/day) is administered starting at least 24 hours (such as 24-72 hours) after microtubule-stabilizing agent administration. In another example, at least 1 mg of pegylated G-CSF (such as 1-10 mg of pegylated G-CSF, for example 6 mg) is administered at least 24 hours (such as 24 hours to 7 days) following MT-stabilizing agent treatment by subcutaneous injection. In a further example, the CSF is GM-CSF. In a particular example, at least 100 µg/m$^2$ of GM-CSF (such as 100-250 µg/m$^2$ of GM-CSF) is administered starting at least 24 hours after microtubule-stabilizing agent administration.

In another example, CSF is administered prior to commencement of treatment with a MT-stabilizing agent. In a particular example, at least 1 µg/kg/day of G-CSF (such as 4-8 µg/kg/day of G-CSF, for example 5 µg/kg/day) is administered starting at least 24 hours (such as 24-72 hours) before MT-stabilizing agent administration. In another example, at least 1 mg of pegylated G-CSF (such as 1-10 mg of pegylated G-CSF, for example 6 mg) is administered at least 24 hours (such as 24 hours to 7 days) before MT-stabilizing agent treatment by subcutaneous injection. In a further example, at least 100 µg/m$^2$ of GM-CSF (such as 100-250 µg/m$^2$ of GM-CSF) is administered starting at least 24 hours before microtubule-stabilizing agent administration.

In a further example, CSF is administered concurrent with treatment with a MT-stabilizing agent. In a particular example, at least 1 µg/kg/day of G-CSF (such as 4-8 µg/kg/day of G-CSF, for example 5 µg/kg/day) is administered starting immediately after the administration of an MT-stabilizing agent. In another example, at least 1 mg of pegylated G-CSF (such as 1-10 mg of pegylated G-CSF, for example 6 mg) is administered starting immediately after the administration of an MT-stabilizing agent by subcutaneous injection. In a further example, at least 100 µg/m$^2$ of GM-CSF (such as 100-250 µg/m$^2$ of GM-CSF) is administered starting immediately after the administration of an MT-stabilizing agent.

Peripheral Neuropathy

The incidence, severity, or duration of peripheral neuropathy in subjects identified to be at increased risk based on ABCB1 genotype can be reduced by additional treatment. In one example, a therapeutically effective amount of amytriptyline is administered to subjects at risk for MT-stabilizing agent-induced peripheral neuropathy, for example before, during, or after administration of the MT-stabilizing agent. In a particular example, at least 5 mg (such as 10-50 mg, for example 25 mg) of amitriptyline is administered at least 24 hours after MT-stabilizing agent administration.

In another example, a therapeutically effective amount of glutamine is administered to subjects at risk for MT-stabilizing-agent-induced peripheral neuropathy for example before, during, or after administration of the MT-stabilizing agent. In a particular example, at least 5 g (such as 5-20 g, for example 10 g) of glutamine is administered orally three times per day, starting at least 24 hours (such as 24-72 hours) following MT-stabilizing agent treatment for at least 1 day (for example 4 days).

In a further example, a therapeutically effective amount of Vitamin E is administered to subjects at risk for MT-stabilizing agent-induced peripheral neuropathy for example before, during, or after administration of the MT-stabilizing agent. In a particular example, at least 100 mg (such as 100-600 mg, for example 300 mg) of Vitamin E is administered orally two times per day starting at the time of administration of MT-stabilizing agent and continuing at least 1 month (such as 1-6 months, for example 3 months) following MT-stabilizing agent treatment.

Diagnostic Reagents

Another aspect of the disclosure includes reagents that can be used to detect one or more ABCB1 polymorphism genotypes in a subject. For example, the disclosed reagents can be used to determine if a subject has one or more polymorphisms at position 1236, 2677 and 3435 of ABCB1 cDNA (e.g. SEQ ID NO: 13), such as a 1236 C>T, 2677 G>T/A or 3435 C>T polymorphism.

Isolated Nucleic Acids

Isolated nucleic acid molecules are provided that in some examples are used to determine the genotype of a subject for polymorphisms in an ABCB1 gene. Exemplary isolated nucleic acids are provided in SEQ ID NOS: 1-12. In one example, an isolated nucleic acid molecule consists of any of SEQ ID NOS: 1-12. However, one skilled in the art will appreciate that minor changes to these sequences will still permit detection of the desired polymorphism in ABCB1. For example, the disclosure provides isolated nucleic acid molecules that include any of SEQ ID NOS: 1-12 containing one or two deletions, substitutions, insertions, or combinations thereof. In a further example, isolated nucleic acid molecules that include, consist essentially of, or consist of SEQ ID NOS: 1-12 can include modified nucleotides, such as nucleotides containing phosphorothioate.

The disclosed isolated nucleic acids can also include one or more detectable labels, for example to permit detection of a nucleic acid molecule. A detectable label is an agent capable of detection, for example by ELISA, spectrophotometry, flow cytometry, or microscopy. For example, a label can be attached to the 5'- or 3'-end of any of SEQ ID NOS: 1-12, or anywhere in between. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (Current Protocols in Molecular Biology, John Wiley & Sons, New York, 1998).

In a particular example, one or more of SEQ ID NOS: 1-6 are used to PCR amplify regions of an ABCB1 gene that contain known polymorphisms (such as 2, 3, 4, 5, or 6 of these sequences). In a further example, one or more of SEQ ID NOS: 7-12 are used to determine the nucleotide sequence of regions of ABCB1 that contain known polymorphisms (such as 2, 3, 4, 5, or 6 of these sequences).

Diagnostic Kits

Kits are provided that can be used to determine if a subject is at an increased risk for MT-stabilizing-agent-induced adverse effects. In one example, the kit contains one or more reagents for detecting at least one polymorphism in an ABCB1 gene. In a particular example, the one or more reagents detect the presence of one or more (such as at least two) of the following polymorphisms: 1236 C>T, 2677G>T/A, or 3435C>T. In another example, the one or more reagents include at least one of the isolated nucleic acids shown in SEQ ID NOS: 1-12, such as 2, 3, 4, 5, 6, 7, 8, 9, 10, 11 or all 12 of these sequences. In one example, the kit includes SEQ ID NOS: 1-6. In another example, the kit includes SEQ ID NOS: 7-12. In yet another example, the kit includes SEQ ID NOS: 1-12.

The disclosed kits can further include other agents, such as buffers, agents that permit amplification of a nucleic acid sequence (such a Taq polymerase or dNTPs), agents that permit sequencing of a nucleic acid sequence (such as fluorescently labeled dideoxynucleotide triphosphates or Taq polymerase), or combinations thereof. In another example the kits can further include agents that permit detection of polymorphisms by TaqMan® assay (such as fluorescently labeled primers or Taq polymerase).

Example 1

Subjects

This example describes the demographics and treatment regimen for the subjects evaluated.

Twenty-six subjects were examined. There were 14 male subjects and 12 female subjects with a median age of 59.5 years (range: 42-72). Details of their demographics are presented in Table 1. The subjects were treated with weekly one- or three-hour paclitaxel infusions. All subjects had histologically proven, locally advanced or metastatic cancer, for which paclitaxel as monotherapy was a therapeutic option.

TABLE 1

Demographics at Baseline

| Characteristic | Value[a] |
|---|---|
| Paclitaxel infusion duration | |
| 1-hour | 12 |
| 3-hours | 14 |
| Site of primary tumor | |
| Breast | 5 |
| Lung | 9 |
| Ovary | 3 |
| Bladder or ureter | 2 |
| Esophagus | 3 |
| Head and neck | 3 |
| Kidney | 1 |
| Prior therapy | 24 |
| Chemotherapy containing vinca | 9 |
| Chemotherapy containing platinum | 14 |
| Radiation therapy | 11 |

[a]Numbers represent number of subjects.

Paclitaxel (30 mg) formulated in a mixture of Cremophor and absolute:ethanol (1:1, vol/vol) (Bristol Myers Squibb, Munich, Germany) was diluted in 500 mL of 5% (weight/vol) dextrose in water and administered to subjects via a peripheral or central venous catheter using a motor-driven programmable infusion pump. Eligible subjects were randomized between a one hour and three hour infusion duration to receive a total of six weekly intravenous infusions of paclitaxel at a dose of 100 mg/m$^2$. After six weeks of therapy (defined as one cycle) response was evaluated bi-dimensionally, usually by computed tomography. Subjects with a stable disease, partial response or complete response after one cycle received a second cycle, provided toxic effects were not prohibitive.

Example 2

Isolation of Nucleic Acids

This example describes methods used to isolate DNA from human plasma.

Genomic deoxyribonucleic acid (DNA) was extracted from 1 mL of human plasma using the QIAamp® Ultrasensitive Virus Kit (Qiagen Inc., Valencia, Calif.), following the manufacturer's instructions. The resulting DNA was reconstituted in a buffer containing 10 mM Tris (pH 7.6) and 1 mM ethylenediamine tetra acetic acid. It will be recognized that additional methods for isolating DNA from human plasma, whole blood, or other biological specimens are well known in the art.

Example 3

Detecting ABCB1 Polymorphisms

This example describes methods used to genotype ABCB1 at positions 1236, 2677 and 3435, relative to the ABCB1 reference coding sequence (CDS) Genbank accession number NM_000927, with the translation start site designated as base position number one. Although a particular method is described, it will be recognized that additional methods for determining the genotype of a subject at a particular position are well known in the art.

For analysis of ABCB1 variants, a 50 μL reaction was prepared for polymerase chain reaction (PCR) amplification using the PCR primer combinations listed in Table 2. The reaction consisted of 1×PCR buffer, 2 mM of each of the four deoxynucleotide triphosphates (dNTPs), 1.5 mM magnesium chloride, and 1 unit of Platinum® Taq DNA polymerase (Invitrogen, Carlsbad, Calif.). PCR conditions were as follows:

94° C. for 5 minutes, followed by 40 cycles of 94° C. for 30 seconds, 68° C. for 30 seconds, and 72° C. for 30 seconds, with a final 7 minute cycle at 72° C. Direct nucleotide sequencing PCR was conducted using the BigDye® Terminator Cycle Sequencing Ready Reaction kit V3.1 (Applied Biosystems, Foster City, Calif., USA) using the sequencing primers listed in Table 2. Sequences were generated on an ABI Prism® 310 Genetic Analyzer. The genotype was called variant if it differed from the consensus sequence of BC130424.

TABLE 2

Primers Used for ABCB1 Amplification and Sequencing

| SNP | PCR Primer Sequence (SEQ ID NO: ) | Sequencing Primer Sequence (SEQ ID NO: ) |
|---|---|---|
| 1236 C > T | F[a] GTTCACTTCAGTT ACCCATCTCG (1) <br> R[b] TATCCTGTCCATCAA CACTGACC (2) | F GTCAGTTCCTATATC CTGTGTCTG (7) <br> R TCCTGTCCATCAACA CTGACCTG (8) |
| 2677 G > A/T | F AGGCTATAGGTTCC AGGCTTGC (3) <br> R AGAACAGTGTGAA GACAATGGCC (4) | F CCCATCATTGCAAT AGCAGGAG (9) <br> R GAACAGTGTGAAGAC AATGGCCT (10) |
| 3435 C > T | F ATCTCACAGTAA CTTGGCAGTTTC (5) <br> R AACCCAAACAGGA AGTGTGGCC (6) | F GCTGGTCCTGAA GTTGATCTGTG (11) <br> R AAACAGGAAGTGTG GCCAGATGC (12) |

[a]Forward primer;
[b]Reverse primer.

All data are reported as median values with the associated 95% confidence interval (95% CI), unless specified otherwise. Genotype-frequency analysis of Hardy-Weinberg equilibrium was carried out using Clump version 1.9. The linkage between each pair of SNPs was determined in terms of the classical statistic D'. The absolute value for D' (|D'|) of 1 denotes complete linkage disequilibrium, while a value of 0 denotes complete linkage equilibrium. All P values are two-tailed, and those less than or equal to 0.05 were considered to reflect statistically significant results.

Genetic analysis was performed to detect ABCB1 SNPs in subjects described in Example 1. As shown in Table 3, the observed ABCB1 genotype frequencies were in Hardy-Weinberg equilibrium (P>0.11), and were similar to previously published values for a predominantly white population. Strong linkage was observed between the three SNPs in ABCB1, with a D' of 1 for the 1236C>T and 2677G>T/A loci (P<0.001); a D' of 0.64 (P=0.007) for the 1236C>T and 3435C>T loci; and a D' of 0.49 for the 2677G>T/A and 3435C>T loci (P=0.042). The most frequently observed haplotypes were T-T-T (40.7%), C-G-C (22.5%), and C-T-C (12.4%), although in total, 6 different haplotypes were observed.

Example 4

Pharmacokinetic Analysis

This example describes analysis of pharmacokinetics of paclitaxel in treated subjects and their association with ABCB1 genotype.

Blood samples were obtained from the subjects described in Example 1 during the first paclitaxel administration at baseline and at serial time points during and after infusion. Concentrations of total paclitaxel in plasma were determined by a validated method based on reversed-phase high performance liquid chromatography with ultraviolet detection, while unbound paclitaxel plasma concentrations were determined by micro-equilibrium dialysis using a [G-$^3$H]paclitaxel tracer. Pertinent pharmacokinetic parameters were calculated by non-compartmental methods using WinNonlin® version 5.0 (Pharsight, Mountain View, Calif., USA).

All data are reported as median values with the associated 95% CI, unless specified otherwise. Interindividual pharmacokinetic variability was assessed as the coefficient of variation, and expressed as a percentage. The associations of the variant genotypes with individual pharmacokinetic parameters were evaluated statistically with the nonparametric Kruskal-Wallis test. All P values are two-tailed, and those less than or equal to 0.05 were considered to reflect statistically significant results.

Pharmacokinetic data for total and unbound paclitaxel were available for all 26 subjects described in Example 1. The parameter describing the time during which concentrations of total paclitaxel in plasma were above 0.05 µM was only available for 25 subjects. As shown in Table 4, none of the studied ABCB1 genotypes were associated with interindividual differences in paclitaxel pharmacokinetic parameters.

TABLE 3

Genotype and Allele Frequencies

| Polymorphism[c] | Effect[d] | Genotype frequencies[a] | | | Allele frequencies[b] | |
|---|---|---|---|---|---|---|
| | | WT[e] | Het | Var | p | q |
| ABCB1 1236C > T | G411G | 5 (19.2%) | 17 (65.4%) | 4 (15.4%) | 0.52 | 0.48 |
| ABCB1 2677G > T | A893S | 2 (7.7%) | 13 (50.0%) | 11 (42.3%) | 0.32 | 0.67 |
| ABCB1 3435C > T | I1145I | 4 (15.4%) | 14 (53.8%) | 8 (30.8%) | 0.42 | 0.58 |

[a]Numbers represent number of subjects with percentage in parentheses; the difference in the total number of subjects is due to the fact that not all samples yielded sequencing data or showed PCR amplification;
[b]Hardy-Weinberg notation for allele frequencies (p, frequency for wild type allele and q, frequency for variant allele);
[c]Number represents position in nucleotide sequence;
[d]Number represents amino acid codon;
[e]WT, Homozygous wild type; Het, Heterozygous; Var, Homozygous variant.

TABLE 4

Association Between ABCB1 Genotype Status and Paclitaxel Pharmacokinetics

| Genotype | T > 0.05 µM (hours) Median (95% CI) | P | AUCp [(ng/mL) × hr] Median (95% CI) | P | AUCu [(ng/mL) × hrs] Median (95% CI) | P |
|---|---|---|---|---|---|---|
| ABCB1 1236C > T | | | | | | |
| Wild-type (N = 5)† | 20.3 (8.8-34.2) | 0.67 | 4657 (2909-9916) | 0.34 | 5007 (371-641) | 0.39 |
| Heterozygous (N = 17) | 15.6 (9.3-19.3)* | | 5264 (3879-6235) | | 470 (445-519) | |
| Variant (N = 4)† | 15.6 (8.8-24.9) | | 3547 (2309-5600) | | 407 (362-522) | |
| ABCB1 2677G > T | | | | | | |
| Wild-type (N = 2)† | 15.1 (8.8-21.3) | 0.97 | 3348 (2909-3787) | 0.18 | 540 (507-572) | 0.26 |
| Heterozygous (N = 13) | 17.3 (9.6-20.7)* | | 5146 (3776-7762) | | 482 (371-641) | |
| Variant (N = 11) | 12.6 (8.8-19.8) | | 4203 (2309-5600) | | 445 (362-516) | |
| ABCB1 3435C > T | | | | | | |
| Wild-type (N = 4)† | 937 (8.8-19.3) | 0.23 | 4534 (2909-5146) | 0.18 | 420 (313-572) | 0.31 |
| Heterozygous (N = 14) | 19.8 (10.5-21.3)* | | 5485 (3787-6344) | | 512 (432-523) | |
| Variant (N = 8) | 13.7 (8.7-18.9) | | 3656 (2259-5600) | | 448 (362-522) | |

*Indicates the genotype of the patient with unavailable T > 0.05 µM data;
†Indicates that 95% confidence intervals are unavailable and the range is quoted instead.
Abbreviations: T > 0.05 µM, duration of total plasma concentration of paclitaxel exceeding 0.05 µM; AUCp, area under the curve of total paclitaxel; AUCu, area under the curve of unbound paclitaxel; 95% CI, 95% confidence interval; P, Kruskal-Wallis test.

Example 5

Association of ABCB1 Genotypes and Neurotoxicity

This example describes the assessment of neurotoxicity in subjects treated with paclitaxel and association of peripheral neuropathy with ABCB1 genotype.

Clinical examination, hematological diagnostics with a complete blood cell count, and the assessment of symptoms and toxicity were performed weekly while subjects described in Example 1 were on paclitaxel therapy. Prior to therapy, and if possible after six and twelve weeks of therapy, these examinations were supplemented by the evaluation of the peripheral neuropathy score, clinical chemistries (serum creatinine, transaminases, alkaline phosphatase, and bilirubin), electrocardiogram analysis and performance status. For the assessment of neurotoxicity a standardized clinical peripheral neuropathy scoring system was used, which included questioning subjects' symptoms, requiring a clinical examination based on a tuning fork test, and an evaluation of strength and peripheral reflexes. This individual clinical score could range from 0 (best) to 12 (worst) points, and based on the inclusion criteria of this trial, peripheral neuropathy was defined as an event when the score exceeded a value of 3 for the first time. A score had to be obtained, at a minimum, prior to and after six and twelve weeks of therapy in order for subjects to be included.

All data are reported as median values with the associated 95% CI, unless specified otherwise. The probability of development of a peripheral neuropathy during paclitaxel therapy as a function of time, according to various genotypes, was analyzed using the Kaplan-Meier method. Statistical significance of the differences between Kaplan-Meier curves was determined using an exact log rank test. All P values are two-tailed, and those less than or equal to 0.05 were considered to reflect statistically significant results.

Twenty-two out of 26 subjects with genetic analyses were assessable for cumulative peripheral neuropathy, while four subjects were excluded due to incorrect infusion durations, impermissible dose reductions, or incomplete follow-up evaluation of the peripheral neuropathy score. Four of these 22 subjects experienced a single event of treatment delay (15 to 21 days) but were still considered eligible for this analysis. No subjects received dose reductions until peripheral neuropathy developed or they were taken off protocol.

Figure 1:
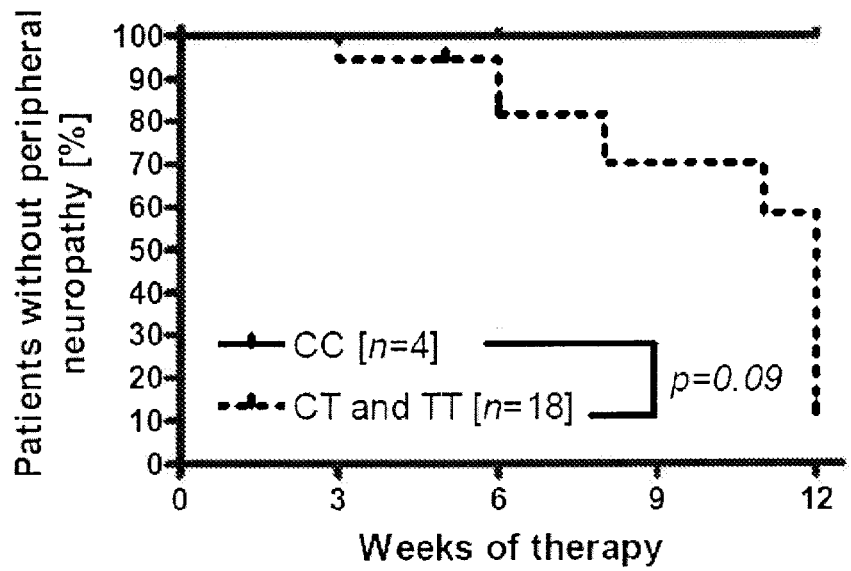
FIG. 1 is a diagram showing the association between the risk of developing grade 3 peripheral neuropathy and ABCB1 genotype status in 22 subjects receiving paclitaxel treatment for 12 weeks. CC, ABCB1 3435CC genotype; CT, ABCB1 3435CT genotype; TT, ABCB1 3435TT genotype. The P value was obtained from an exact two-tailed log rank test.

As shown in FIG. 1, subjects carrying the ABCB1 3435CT or ABCB1 3435TT genotype were more likely to develop clinically significant cumulative peripheral neuropathy. The four subjects wild-type for the ABCB1 3435C>T transition did not develop peripheral neuropathy during the observation period, whereas 17 of 18 subjects carrying at least one variant allele at this position developed peripheral neuropathy. This trend approached statistical significance (P=0.09) using an exact log-rank test, unadjusted for multiple comparisons. Variant alleles were grouped based on previous observations that ABCB1 expression and activity are decreased in subjects carrying at least one ABCB1 3435T allele. Although the above data are not statistically significant, most likely due to the small sample size, it is still notable that no subjects carrying the ABCB1 3435CC (wild type) genotype developed peripheral neuropathy, whereas those subjects heterozygous or homozygous variant for this allele had a much greater propensity to develop this side effect during treatment. Similar associations were not observed for the ABCB1 2677G>T (P=0.85) genotype, or any of the haplotypes (P>0.05).

These results demonstrate that the ABCB1 3435C>T polymorphism has predictive power in the assessment of ABCB1 expression and activity at the blood-nerve barrier, and thus, taxane-induced peripheral neuropathy.

Example 6

Association of ABCB1 Genotypes and Myelotoxicity

This example describes the assessment of myelotoxicity in subjects treated with paclitaxel and association of neutropenia with ABCB1 genotype.

Clinical examination, hematological diagnostics with a complete blood cell count, as well as the assessment of symptoms and toxicity were performed weekly while subjects described in Example 1 were on paclitaxel therapy. Hematological requirements for paclitaxel administration were an absolute neutrophil count $\geq 1.5 \times 10^9$/L and a platelet count $\geq 75 \times 10^9$/L. Toxicities other than peripheral neuropathy were graded according to the National Cancer Institute common toxicity criteria guidelines, version 2.0.

All data are reported as median values with the associated 95% CI, unless specified otherwise. Hematological pharmacodynamics were evaluated by analysis of the absolute nadir values of neutrophil counts relative to the baseline value between days 1 and 36, and was expressed as a percentage. The associations of the variant genotypes with neutropenia were evaluated statistically with the nonparametric Kruskal-Wallis test. An exact Wilcoxon rank sum test was used to determine the statistical significance of the difference in percent absolute neutrophil count decline between subjects with a 2677/3435 diplotype double variant and the other subjects. It was reported after a Bonferroni adjustment to correct for an evaluation of a set of four hematologic parameters, as well as a pooling of diplotypes following an exploratory analysis.

Complete sets of neutrophil counts within the first six weeks of treatment were available for 19 out of the 26 subjects. One further patient had to be excluded due to incorrect infusion duration so that ultimately 18 subjects remained assessable for myelotoxicity analysis. Three of these 18 subjects had a single delay in their treatment delivery of 15 to 21 days but were still included. As shown in FIG. 2, consideration of four hematologic parameters, including total platelet/neutrophil counts at nadir, and percent decreases of platelet or neutrophil counts at nadir, demonstrated a significant association between the percent decrease from baseline in neutrophil count at nadir and the ABCB1 2677/3435 variant diplotype. Specifically, subjects variant at both the 2677 and 3435 loci demonstrated an approximately 1.5-fold greater percent decrease (P=0.02, after a conservative adjustment) in neutrophil count at nadir (median: 79.7%, range: 74.2-83.1, n=3) as compared to the rest of the population (median: 53.8%; range: 27.5%-73.7%, n=15). Variant alleles were grouped on the notion that both the 2677 and 3435 loci were recently determined to be important determinants of ABCB1 expression. This particular diplotype was unrelated to any of the studied pharmacokinetic parameters in the 26 subjects wherein pharmacokinetic data were available (P>0.05).

These results demonstrate that the 2677G>T/A and 3435C>T alleles in combination are able to predict the expression and activity of ABCB1 in repopulating neutrophils and thus, the likelihood of neutropenia in response to taxane chemotherapy.

Example 7

Association of ABCB1 Genotypes and Neurotoxicity

This example describes the assessment of neurotoxicity in subjects treated with docetaxel and association of peripheral neuropathy with ABCB1 genotype.

ABCB1 genotypes were evaluated in patients from a trial involving 73 men with androgen-independent prostate cancer that were treated with either docetaxel alone or docetaxel in combination with thalidomide. Patients were administered docetaxel intravenously (30 mg/m2) over 1 hour every week for 3 consecutive weeks (n=23). Some patients additionally received 200 mg of thalidomide orally each day (n=50). Toxicity was defined by Cancer Therapy Evaluation Program/National Cancer Institute Common Toxicity Criteria (version 2.0) and patients were evaluated for symptoms of toxicity weekly.

As shown in FIG. 3, there is a clear difference in the time to onset of peripheral neuropathy in subjects treated with docetaxel based on the ABCB1 2677GG vs 2677GT and 2677TT genotypes. Subjects carrying the ABCB1 2677GT, 2677TT or 2677GA genotype were more likely to develop clinically significant cumulative peripheral neuropathy. Of the 15 subjects wild-type for the ABCB1 2677G>T/A transition, 4 did not develop peripheral neuropathy during the observation period, whereas 3 of 35 subjects carrying at least one variant allele at this position did not. Of the 15 subjects wild-type for the ABCB1 2677G>T/A transition, 11 developed peripheral neuropathy during the observation period, whereas 32 of 35 subjects carrying at least one variant allele at this position developed peripheral neuropathy. This trend was statistically significant (p=0.017) using an exact log-rank test, adjusted for multiple comparisons.

As shown in Table 5, there is also a trend towards an association with double variant 2677TT+3435TT, versus all other of the ABCB1 polymorphisms at positions 1236, 2677, and 3535 and increased clinical grade of neutropenia (p=0.053 following a conservative adjustment for multiple comparisons).

TABLE 5

Association of ABCB1 Polymorphisms and Clinical Grade of Neutropenia

| | # Patients with Clinical Grade of Neutropenia | | | | |
|---|---|---|---|---|---|
| Genotype | Grade 0 | Grade 2 | Grade 3 | Total Patients | P-value* |
| 2677TT + 3435TT | 8 | 0 | 3 | 11 | 0.053 |
| Other ABCB1 Genotypes | 35 | 3 | 1 | 39 | |

*P-value determined by the Cochran-Armitage Trend Test

Example 8

Association of ABCB1 Genotype with Neurotoxicity and Myelotoxicity Following Epothilone Treatment This example describes the assessment of myelotoxicity and neurotoxicity in subjects treated with ixabepilone and association of neutropenia and peripheral neuropathy with ABCB1 genotype.

Subjects will receive ixabepilone (BMS-247550) as treatment for breast cancer. Subjects will receive infusions of ixabepilone at 6 mg/m$^2$/day over one hour daily for five days every three weeks or infusions of ixabepilone at 8 mg/m$^2$/day over one hour daily for three days every three weeks. Subjects may also receive an infusion of ixabepilone at 35-40 mg/m$^2$ over three hours every three weeks. DNA will be isolated as described in Example 2. ABCB1 genotype will be determined as described in Example 3. Subjects will be assessed for development of peripheral neuropathy as described in Examples 5 and 7 and neutropenia as described in Example 6 during the course of ixabepilone treatment.

Example 9

ABCB1 Genotyping and MT-Stabilizing Agent Treatment

This example describes treatment decisions that can be made based on the ABCB1 genotype of a subject who is undergoing treatment with a MT-stabilizing agent.

DNA will be isolated from subjects as described in Example 2 or other suitable methods. The genotype for ABCB1 polymorphisms will be determined as described in Example 3, or other methods known in the art.

If a subject is found to have the ABCB1 genotype of 3435CT or 3435TT, it is concluded that the subject has an increased risk of developing at least one or more MT-stabilizing agent-induced adverse effects, such as peripheral neuropathy, following treatment with a MT-stabilizing agent. In this situation, the treatment regimen can be modified to decrease the likelihood of occurrence or severity of peripheral neuropathy. This can include, but is not limited to, decreasing the dosage of MT-stabilizing agent (for example decreasing the dosage by at least 20%, such as at least 50%), increasing the interval between doses of MT-stabilizing agent (for example increasing the interval by at least one day, at least seven days, at least fourteen days, or even at least 30 days), increasing the time over which a dose of MT-stabilizing agent is administered (for example by at least 1 hr, at least 12 hrs, or at least 24 hrs), or combinations thereof.

If the subject is found to have the ABCB1 double variant phenotype at both positions 2677 and 3435, it is concluded that the subject has an increased of developing at least one or more MT-stabilizing agent-induced adverse effects, such as neutropenia, following treatment with a microtubule-stabilizing agent. In this situation, the treatment regimen can be modified to decrease the likelihood of occurrence of neutropenia. This can include, but is not limited to, decreasing the dosage of MT-stabilizing agent, increasing the interval between doses of MT-stabilizing agent, increasing the time over which a dose of MT-stabilizing agent is administered (for example as described above), administering at least one therapeutically effective amount dose of CSF following administration of MT-stabilizing agent, or combinations thereof.

In contrast, if the subject is found to have wild-type ABCB1 genotype at positions 2677 and 3435, it is concluded that the subject does not have an increased of developing at least one or more MT-stabilizing agent-induced adverse effects, and thus administration of MT-stabilizing agent (such as a taxane) need not be modified.

Example 10

Accumulation of Paclitaxel in Peripheral Neurons of ABCB1 Knockout Mice

This example describes methods that can be used to assess the accumulation of paclitaxel in peripheral neurons of mice that lack expression of ABCB1. Mice that lack expression of ABCB1 (such as mdr1a −/− mice or mdr1b −/− mice) can be used to evaluate the differential accumulation of paclitaxel in peripheral neurons based on the level of ABCB1 expression. 10-30 mg/kg of paclitaxel will be administered intravenously to wild type and control mice. [$^{14}$C]paclitaxel will be administered, and accumulation of paclitaxel in peripheral nervous tissue will be monitored by digital whole body autoradiography at subsequent time points, such as 1 hour, 3 hours, or 24 hours following administration Likewise, fluorescently-labeled paclitaxel will be administered to mice and uptake by peripheral neurons will be monitored by fluorescent microscopy at subsequent time points, such as 1 hour, 3 hours, or 24 hours following administration. These experiments will confirm that a decrease in expression of ABCB1 in peripheral neurons results in increased accumulation of paclitaxel in this tissue.

In view of the many possible embodiments to which the principles of the disclosed examples may be applied, it should be recognized that the illustrated embodiments are only preferred examples of the invention and should not be taken as limiting the scope of the invention. Rather, the scope of the disclosure is defined by the following claims. We therefore claim as our invention all that comes within the scope and spirit of these claims.

We claim:

1. A method for identifying a human subject at increased risk for developing microtubule-stabilizing-agent-induced adverse effects selected from the group consisting of neutropenia and peripheral neuropathy, comprising:
   amplifying DNA isolated from a biological sample obtained from a human subject having a tumor that can be treated with a microtubule-stabilizing-agent or a subject who has been treated with a microtubule-stabilizing-agent using primer sequences selected from the group consisting of SEQ ID NOS: 3, 4, 5 and 6;
   determining in a biological sample obtained from a human subject having a tumor that can be treated with a microtubule-stabilizing-agent or a subject who has been treated with a microtubule-stabilizing-agent that the human subject has a 2677G>T (Ala893Ser) and a 3435C>T (synonymous) predictive polymorphism in an ABCB1 gene, wherein the primer sequences consisting of SEQ ID NOS: 9 and 10 are used to detect 2677G>T and the primer sequences consisting of SEQ ID NOS: 11 and 12 are used to detect 3435C>T; and
   identifying the subject as one at increased risk for developing microtubule-stabilizing agent-induced adverse effects selected from the group consisting of neutropenia and peripheral neuropathy as compared to a subject which does not have the 2677G>T (Ala893Ser) and 3435C>T (synonymous) predictive polymorphisms.

2. The method of claim 1, wherein the microtubule-stabilizing agent comprises an epothilone.

3. The method of claim 2, wherein the epothilone comprises ixabepilone.

4. The method of claim 1, wherein the microtubule-stabilizing agent comprises a taxane.

5. The method of claim 4, wherein the taxane comprises paclitaxel (Taxol®), docetaxel (Taxotere®), or an analog of paclitaxel.

6. The method of claim 1, wherein the subject has a disease that is sensitive to administration of a therapeutically effective amount of a microtubule-stabilizing agent.

7. The method of claim 6, further comprising:
   administering to the subject a therapeutically effective amount of a microtubule-stabilizing agent.

8. The method of claim 7, wherein the effective amount of a microtubule-stabilizing agent is less than 100 mg/m$^2$.

9. The method of claim 1, further comprising:
   obtaining a blood sample from the subject; and
   isolating DNA from the blood sample, wherein determining that the human subject has the predictive polymorphisms in the ABCB1 gene comprises determining whether the isolated DNA comprises the predictive polymorphisms in the ABCB1 gene.

10. The method of claim 9, wherein the blood sample is a plasma sample.

11. A method for decreasing occurrence of microtubule-stabilizing-agent-induced adverse effects selected from the group consisting of neutropenia and peripheral neuropathy in a human subject having a disorder which can be treated with a therapeutically effective amount of a microtubule-stabilizing agent, comprising:
   amplifying DNA isolated from a biological sample obtained from a human subject having a tumor that can be treated with a microtubule-stabilizing-agent or a subject who has been treated with a microtubule-stabilizing-agent using primer sequences selected from the group consisting of SEQ ID NOS: 3, 4, 5 and 6;
   determining in a biological sample obtained from a human subject having a tumor that can be treated with a microtubule-stabilizing-agent or a subject who has been treated with a microtubule-stabilizing-agent that the human subject has a 2677G>T (Ala893Ser) and a 3435C>T (synonymous) predictive polymorphism in an ABCB1 gene, wherein the primer sequences consisting of SEQ ID NOS: 9 and 10 are used to detect 2677G>T and wherein the primer sequences consisting of SEQ ID NOS: 11 and 12 are used to detect 3435C>T; and
   modifying administration of a microtubule-stabilizing agent to decrease microtubule-stabilizing-agent-induced adverse effects selected from the group consisting of neutropenia and peripheral neuropathy to the human subject having the predictive polymorphisms.

12. The method of claim 11, wherein the amount of microtubule-stabilizing agent administered is decreased, an interval between microtubule-stabilizing agent administration is increased, a dosing schedule of microtubule-stabilizing agent administration is increased, a therapeutically effective amount of colony-stimulating factor is administered, or combinations thereof.

13. The method of claim 12, wherein the colony-stimulating factor comprises granulocyte colony-stimulating factor or granulocyte macrophage colony-stimulating factor.

14. The method of claim 11, wherein microtubule-stabilizing agent dosage is decreased, timing of microtubule-stabilizing agent administration is altered, dosing schedule of microtubule-stabilizing agent administration is increased, or combinations thereof.

* * * * *